(12) United States Patent
Ziv

(10) Patent No.: US 8,727,961 B2
(45) Date of Patent: May 20, 2014

(54) APPARATUS FOR THE PREVENTION OF URINARY INCONTINENCE IN FEMALES

(75) Inventor: Elan Ziv, Ramat-Gan (IL)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 910 days.

(21) Appl. No.: 10/598,872

(22) PCT Filed: Mar. 17, 2005

(86) PCT No.: PCT/IL2005/000304
§ 371 (c)(1),
(2), (4) Date: May 18, 2007

(87) PCT Pub. No.: WO2005/087154
PCT Pub. Date: Sep. 22, 2005

(65) Prior Publication Data
US 2007/0244352 A1 Oct. 18, 2007

Related U.S. Application Data

(63) Continuation-in-part of application No. 10/557,865, filed as application No. PCT/IL2004/000433 on May 20, 2004, now Pat. No. 7,771,344.

(60) Provisional application No. 60/553,964, filed on Mar. 18, 2004, provisional application No. 60/555,977, filed on Mar. 25, 2004, provisional application No. 60/570,469, filed on May 13, 2004, provisional application No. 60/570,535, filed on May 13, 2004, provisional application No. 60/598,835, filed on Aug. 5, 2004, provisional application No. 60/602,636, filed on Aug. 19, 2004.

(30) Foreign Application Priority Data

May 22, 2003 (IL) .......................................... 156070
Jul. 27, 2003 (IL) .......................................... 157117

(51) Int. Cl.
*A61F 6/08* (2006.01)

(52) U.S. Cl.
USPC ............................................. 600/29; 128/834

(58) Field of Classification Search
USPC ......................... 600/29–30, 37; 128/830–841
See application file for complete search history.

(56) References Cited

U.S. PATENT DOCUMENTS 2,141,040 A 12/1938 Iiolt
(Continued)

FOREIGN PATENT DOCUMENTS

DE 271657 3/1914
(Continued)

OTHER PUBLICATIONS

International Preliminary Report on Patentability Dated Dec. 8, 2009 From the International Preliminary Examining Authority Re.: Application No. PCT/IL2008/001292.
(Continued)

*Primary Examiner* — Charles A Marmor II
*Assistant Examiner* — Catherine E Burk
(74) *Attorney, Agent, or Firm* — Kimberly-Clark Worldwide, Inc.

(57) ABSTRACT

An apparatus for treating urinary incontinence, comprising a node; a support section adapted for providing urethral support attached to the node; and, an anchoring section adapted for resisting movement of the apparatus attached to the node; wherein the node is no longer than 30% of the entire length of the apparatus comprising the node, support section and the anchoring section together.

5 Claims, 19 Drawing Sheets

(56) References Cited

U.S. PATENT DOCUMENTS

| | | |
|---|---|---|
| 2,146,574 A | 2/1939 | Iiay |
| 2,432,768 A | 12/1947 | Kurkjian |
| 2,938,519 A | 5/1960 | Marco |
| 3,138,159 A | 6/1964 | Schmidt |
| 3,646,929 A | 3/1972 | Bonnar |
| 3,683,906 A | 8/1972 | Robinson |
| 3,789,828 A | 2/1974 | Schulte |
| 3,797,478 A | 3/1974 | Walsh et al. |
| 3,841,304 A | 10/1974 | Jones |
| 4,019,498 A | 4/1977 | Hawtrey |
| 4,019,499 A | 4/1977 | Fitzgerald |
| 4,139,006 A | 2/1979 | Corey |
| 4,142,649 A | 3/1979 | Forgey |
| 4,212,301 A | 7/1980 | Johnson |
| 4,307,716 A | 12/1981 | Davis |
| 4,428,365 A | 1/1984 | Hakky |
| 4,457,299 A | 7/1984 | Cornwell |
| 4,553,533 A | 11/1985 | Leighton |
| 4,726,805 A | 2/1988 | Sanders |
| 4,823,814 A | 4/1989 | Drogendijk et al. |
| 4,846,784 A | 7/1989 | Haber |
| 4,850,963 A | 7/1989 | Sparks et al. |
| 4,920,986 A | 5/1990 | Biswas |
| 5,007,894 A | 4/1991 | Enhorning |
| 5,014,722 A | 5/1991 | Bauer |
| 5,036,867 A | 8/1991 | Biswas |
| 5,041,077 A | 8/1991 | Kulick |
| 5,090,424 A | 2/1992 | Simon et al. |
| 5,224,493 A | 7/1993 | Sawan et al. |
| 5,224,494 A | 7/1993 | Enhorning |
| 5,336,208 A | 8/1994 | Rosenbluth et al. |
| 5,352,182 A | 10/1994 | Kalb et al. |
| 5,370,657 A | 12/1994 | Irie |
| 5,386,836 A | 2/1995 | Biswas |
| 5,417,226 A | 5/1995 | Juma |
| 5,483,976 A | 1/1996 | McLaughlin et al. |
| 5,603,685 A | 2/1997 | Tutrone, Jr. |
| 5,609,586 A | 3/1997 | Zadini et al. |
| 5,618,256 A * | 4/1997 | Reimer .......................... 600/29 |
| 5,659,934 A | 8/1997 | Jessup et al. |
| 5,671,755 A | 9/1997 | Simon et al. |
| 5,724,994 A | 3/1998 | Simon et al. |
| 5,755,906 A | 5/1998 | Achter et al. |
| 5,771,899 A | 6/1998 | Martelly et al. |
| 5,782,745 A | 7/1998 | Benderev |
| 5,785,640 A * | 7/1998 | Kresch et al. .................. 600/29 |
| 5,788,664 A | 8/1998 | Scalise |
| 5,795,346 A | 8/1998 | Achter et al. |
| 5,894,842 A | 4/1999 | Rabin et al. |
| 6,013,023 A | 1/2000 | Klingenstein |
| 6,090,038 A | 7/2000 | Zunker et al. |
| 6,090,098 A | 7/2000 | Zunker et al. |
| 6,142,928 A | 11/2000 | Zunker et al. |
| 6,158,435 A | 12/2000 | Dorsey |
| 6,189,535 B1 | 2/2001 | Enhorning |
| 6,216,698 B1 | 4/2001 | Regula |
| 6,251,122 B1 | 6/2001 | Tsukernik |
| 6,413,206 B2 | 7/2002 | Biswas |
| 6,415,484 B1 | 7/2002 | Moser |
| 6,418,930 B1 | 7/2002 | Fowler |
| 6,428,467 B1 | 8/2002 | Benderev |
| 6,458,072 B1 | 10/2002 | Zunker |
| 6,460,542 B1 | 10/2002 | James |
| 6,461,215 B1 | 10/2002 | Kunz et al. |
| 6,478,726 B1 | 11/2002 | Zunker |
| 6,503,190 B1 | 1/2003 | Ulmsten et al. |
| 6,558,370 B2 | 5/2003 | Moser |
| 6,645,136 B1 | 11/2003 | Zunker et al. |
| 6,676,594 B1 | 1/2004 | Zunker et al. |
| 6,679,831 B1 | 1/2004 | Zunker et al. |
| 6,739,340 B1 | 5/2004 | Jensen et al. |
| 6,770,025 B2 | 8/2004 | Zunker |
| 6,808,485 B2 | 10/2004 | Zunker |
| 7,036,511 B2 | 5/2006 | Nissenkorn |
| 7,717,892 B2 * | 5/2010 | Bartning et al. .............. 604/329 |
| 7,931,671 B2 | 4/2011 | Tenerz |
| 8,435,168 B2 | 5/2013 | Ziv et al. |
| 2002/0068023 A1 | 6/2002 | Davis |
| 2002/0083949 A1 | 7/2002 | James |
| 2002/0115906 A1 | 8/2002 | Miller |
| 2002/0120243 A1 | 8/2002 | Kraemer et al. |
| 2002/0138035 A1 | 9/2002 | Hull, Jr. |
| 2002/0156341 A1 | 10/2002 | Zunker |
| 2002/0156343 A1 | 10/2002 | Zunker |
| 2002/0183711 A1 | 12/2002 | Moser |
| 2003/0149334 A1 | 8/2003 | Ulmsten et al. |
| 2003/0149392 A1 | 8/2003 | Arnould |
| 2004/0054252 A1 | 3/2004 | Zunker |
| 2004/0078013 A1 | 4/2004 | Zunker et al. |
| 2004/0084054 A1 | 5/2004 | Kaseki et al. |
| 2004/0122285 A1 | 6/2004 | Zunker |
| 2004/0158122 A1 | 8/2004 | Guerquin |
| 2004/0199100 A1 | 10/2004 | LeMay et al. |
| 2005/0016545 A1 | 1/2005 | Nissenkorn |
| 2006/0100475 A1 | 5/2006 | White et al. |
| 2007/0088189 A1 | 4/2007 | Levy |
| 2007/0203429 A1 | 8/2007 | Ziv |
| 2007/0244352 A1 | 10/2007 | Ziv |
| 2008/0149109 A1 | 6/2008 | Ziv |
| 2008/0281149 A1 | 11/2008 | Sinai et al. |
| 2009/0266367 A1 | 10/2009 | Ziv et al. |
| 2009/0283099 A1 | 11/2009 | Harmanli |
| 2011/0065980 A1 | 3/2011 | Ziv et al. |
| 2012/0271098 A1 | 10/2012 | Ziv et al. |
| 2013/0165743 A1 | 6/2013 | Ziv et al. |

FOREIGN PATENT DOCUMENTS

| | | | |
|---|---|---|---|
| DE | 19816349 | 10/1999 | |
| EP | 0264258 | 4/1988 | |
| EP | 0274762 | 7/1988 | |
| EP | 0933069 | 8/1988 | |
| EP | 0700669 | 3/1996 | |
| EP | 0921778 | 6/1999 | |
| EP | 0955024 | 11/1999 | |
| EP | 1139963 | 10/2001 | |
| EP | 1139962 | 5/2005 | |
| EP | 1727491 | 12/2006 | |
| FR | 2843700 | 2/2004 | |
| GB | 1115727 | 5/1968 | |
| GB | 2352181 | 1/2001 | |
| GB | 2384436 | 7/2003 | |
| JP | 63-177852 | 7/1988 | |
| JP | 03-500489 | 2/1991 | |
| JP | 06-133996 | 5/1994 | |
| JP | 06-503982 | 5/1994 | |
| JP | 61-33996 | 5/1994 | |
| JP | 09-501595 | 2/1997 | |
| JP | 2001-502929 | 3/2001 | |
| JP | 2002-532198 | 2/2002 | |
| JP | 2002-5332199 | 10/2002 | |
| WO | WO 88/10106 | 12/1988 | |
| WO | WO 89/09582 | 10/1989 | |
| WO | WO 95/05790 | 3/1995 | |
| WO | WO 96/01084 | 1/1996 | |
| WO | WO 97/34550 | 9/1997 | |
| WO | WO 9849980 A1 * | 11/1998 | ................ A61F 5/48 |
| WO | WO 00/03659 | 1/2000 | |
| WO | WO 00/36996 | 6/2000 | |
| WO | WO 00/67662 | 11/2000 | |
| WO | WO00/67662 A1 * | 11/2000 | ................ A61F 2/00 |
| WO | WO 02/26160 | 4/2002 | |
| WO | WO 02/089704 | 11/2002 | |
| WO | WO 03/047476 | 6/2003 | |
| WO | WO 2004/000433 | 12/2003 | |
| WO | WO 2004/103213 | 12/2004 | |
| WO | WO 2005/087153 | 9/2005 | |
| WO | WO 2005/087154 | 9/2005 | |
| WO | WO 2006/097935 | 9/2006 | |
| WO | WO 2008/010214 | 1/2008 | |
| WO | WO 2008/079271 | 7/2008 | |
| WO | WO 2008/152628 | 12/2008 | |

(56) References Cited

FOREIGN PATENT DOCUMENTS

| WO | WO 2009/044394 | 4/2009 |
|---|---|---|
| WO | WO 2009/130702 | 10/2009 |

OTHER PUBLICATIONS

International Preliminary Report on Patentability Dated Oct. 14, 2008 From the International Preliminary Examining Authority Re.: Application No. PCT/IL06/00346.
International Search Report and the Written Opinion Dated Oct. 26, 2005 From the International Searching Authority Re.: Application No. PCT/IL2005/000303.
Official Action Dated Oct. 15, 2009 From the US Patent and Trademark Office Re.: U.S. Appl. No. 10/557,865.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Written Opinion Dated May 23, 2006 From the International Preliminary Examining Authority Re.: Application No. PCT/IL2005/000303.
Communication Pursuant to Article 94(3) EPC Dated Apr. 16, 2009 From the European Patent Office Re.: Application No. 05718876.5.
Communication Relating to the Results of the Partial International Search Dated Dec. 7, 2007 From the International Searching Authority Re.: Application No. PCT/IL2007/000893.
Communication Relating to the Results of the Partial international Search Dated Jan. 12, 2009 From the International Searching Authority Re.: Application No. PCT/IL2008/001292.
Communiction Pursuant to Article 94(3) EPC Dated Apr. 16, 2009 From the European Patent Office Re.: Application No. 05718877.3.
Examiner's Report Dated Dec. 9, 2009 From the Australian Government, IP Australia Re.: Application No. 2005221424.
International Preliminary Report on Patentability Dated Dec. 23, 2009 From the International Bureau of WIPO Re.: Application No. PCT/IL2008/000786.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report and the Written Opinion Dated Oct. 28, 2009 From the International Searching Authority Re.: Application No. PCT/IL2009/000443.
International Search Report Dated Mar. 25, 2009 From the International Searching Authority Re.: Application No. PCT/IL2008/001292.
Notice of Allowance Dated Mar. 31, 2010 From the US Patent and Trademark Office Re.: U.S. Appl. No. 10/557,865.
Office Action Dated Jan. 18, 2010 From the Israel Patent Office Re.: Application No. 156070 and Its Translation Into English.
Official Action Dated Apr. 17, 2009 From the Patent Office of the Russian Federation Re.: Application No. 2006136791 and Its Translation Into English.
Official Action Dated Feb. 19, 2010 From the US Patent and Trademark Office Re.: U.S. Appl. No. 10/593,367.
Response Dated Mar. 15, 2010 to Official Action of Oct. 15, 2009 From the US Patent and Trademark Office Re.: U.S. Appl. No. 10/557,865.
Response Dated Feb. 22, 2010 to International Search Report and the Written Opinion of Oct. 28, 2009 From the International Searching Authority Re.: Application No. PCT/IL2009/000443.
Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.
Translation of Office Action Dated Jan. 19, 2010 From the State Intellectual Property Office of the People's Republic of China Re.: Application No. 200680017262.2.

Written Opinion Dated Mar. 25, 2009 From the International Searching Authority Re.: Application No. PCT/IL2008/001292.
Translation of Notification of Reasons of Rejection Dated Apr. 8, 2010 From the Japanese Patent Office Re.: Application No. 2007-503494.
Notification Dated Dec. 17, 2008 From the Russian Patent Office Re.: Application No. 2006136791 and Its Translation Into English.
Office Action Dated Jan. 9, 2009 From the State Intellectual Property Office of the People's Republic of China Re.: Application No. 200580016245.2 and Its Translation Into English.
Official Action Dated Mar. 6, 2009 From the US Patent and Trademark Office Re.: U.S. Appl. No. 10/557,865.
Supplemental Notice of Allowability Dated Apr. 27, 2010 From the US Patent and Trademark Office Re.: U.S. Appl. No. 10/557,865.
Communication Pursuant to Article 94(3) EPC Dated Mar. 23, 2010 From the European Patent Office Re.: Application No. 05718876.5.
Translation of Notification of Reasons for Rejection Dated Jun. 1, 2010 From the Japanese Patent Office Re. Application No. 2006-531002.
Response Dated Jun. 21, 2010 to Office Action of Jan. 29, 2010 From the State Intellectual Property Office of the People's Republic of China Re.: Application No. 200680017262.2.
Official Action Dated Jun. 23, 2010 From the US Patent and Trademark Office Re.: U.S. Appl. No. 10/593,367.
Second Supplemental Notice of Allowability Dated Jun. 3, 2010 From the US Patent and Trademark Office Re.: U.S. Appl. No. 10/557,865.
Official Action Dated Jun. 11, 2010 From the Federal Institute of Industrial and Intellectual Property, Patents and Trademarks, ROSPATENT, of the Russian Federation Re.: Application No. 2010100368 and Its Summary Into English.
Communiction Pursuant to Article 94(3) EPC Dated Jul. 2, 2010 From the European Patent Office Re.: Application No. 05718877.3.
International Preliminary Report on Patentability Dated Jul. 15, 2010 From the International Preliminary Examining Authority Re.: Application No. PCT/IL2009/000443.
Response Dated Aug. 1, 2010 to Notification of Reasons of Rejection Dated Apr. 8, 2010 From the Japanese Patent Office Re.: Application No. 2007-503494.
Response Dated Aug. 30, 2010 to Notification of Reasons for Rejection of Jun. 1, 2010 From the Japanese Patent Office Re. Application No. 2006-531002.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
European Search Report Under Rule 112 EPC Dated Dec. 27, 2007 From the European Patent Office Re.: Application No. 05718876.5.
International Preliminary Report on Patentability Dated Jul. 6, 2006 From the International Preliminary Examining Authority Re.: Application No. PCT/IL2005/000304.
International Search Report Dated Dec. 11, 2006 From the International Searching Authority Re.: Application No. PCT/IL06/00346.
International Search Report Dated Apr. 14, 2008 From the International Searching Authority Re.: Application No. PCT/IL2007/000893.
International Search Report Dated Sep. 23, 2005 From the International Searching Authority Re.: Application No. PCT/IL2005/000304.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated Sep. 23, 2005 From the International Searching Authority Re.: Application No. PCT/IL2005/000304.
Response Dated Nov. 3, 2010 to Communication Pursuant to Article 94(3) EPC of Jul. 2, 2010 From the European Patent Office Re. Application No. 057188877.3.
Examiner's Report Dated Dec. 15, 2010 From the Australian Government, IP Australia Re.: Application No. 2005221424.

(56) References Cited

OTHER PUBLICATIONS

Examiner's Report Dated Nov. 29, 2010 From the Australian Government, IP Australia Re. Application No. 2006224158.
Response Dated Dec. 8, 2010 to Examiner's Report of Dec. 9, 2009 From the Australian Government, IP Australia Re.: Application No. 2005221424.
Response Dated Nov. 16, 2010 to Office Action of Sep. 17, 2010 From the State Intellectual Property Office of the People's Republic of China Re.: Application No. 200680017262.2.
Response Dated Oct. 20, 2010 to Official Action of Jun. 11, 2010 From the Federal Institute of Industrial and Intellectual Property, Patents and Trademarks, ROSPATENT, of the Russian Federation Re.: Application No. 2010100368.
Response Dated Sep. 30, 2010 to Communication Pursuant to Article 94(3) EPC of Mar. 23, 2010 From the European Patent Office Re.: Application No. 05718876.5.
Translation of Notification of Reasons for Rejection Dated Dec. 24, 2010 From the Japanese Patent Office Re. Application No. 2007-503495.
Translation of Office Action Dated Sep. 17, 2010 From the State Intellectual Property Office of the People's Republic of China Re.: Application No. 200680017262.2.
Official Action Dated Dec. 28, 2010 From the US Patent and Trademark Office Re.: U.S. Appl. No. 10/593,367.
Response Dated Oct. 25, 2010 to Official Action of Jun. 23, 2010 From the US Patent and Trademark Office Re.: U.S. Appl. No. 10/593,367.
Examiner-Initiated Interview Summary Dated Oct. 10, 2012 From the US Patent and Trademark Office Re. U.S. Appl. No. 12/680,575.
Notice of Allowance Dated Jan. 7, 2013 From the US Patent and Trademark Office Re. U.S. Appl. No. 12/373,937.
Office Action Dated Dec. 5, 2012 From the Israel Patent Office Re. Application No. 176883 and Its Translation Into English.
Notice of Acceptance Dated Feb. 2, 2011 From the Australian Government, IP Australia Re.: Application No. 2005221424.
Examination Report Dated Jan. 16, 2012 From the Instituto Mexicano de la Propriedad Industrial Re. Application No. PA/a/2006/010653 and Its Summary in English.
Official Action Dated Feb. 15, 2012 From the US Patent and Trademark Office Re. U.S. Appl. No. 12/373,937.
Restriction Official Action Dated Feb. 28, 2012 From the US Patent and Trademark Office Re. U.S. Appl. No. 11/886,248.
Decision to Refuse a European Patent Application Dated Feb. 25, 2013 From the European Patent Office Re. Application No. 04734069.0.
Requisition by the Examiner Dated Feb. 19, 2013 From the Canadian Intellectual Property Office Re. Application No. 2,560,877.
Restriction Official Action Dated Feb. 6, 2013 From the US Patent and Trademark Office Re. U.S. Appl. No. 12/663,714.
Official Action Dated Feb. 9, 2011 From the US Patent and Trademark Office Re.: U.S. Appl. No. 10/593,367.
Communication Pursuant to Article 94(3) EPC Dated Feb. 4, 2011 From the European Patent Office Re. Application No. 04734069.0.
Communication Relating to the Results of the Partial International Search Dated Mar. 3, 2011 From the International Searching Authority Re. Application No. PCT/IL2010/000985.
Notification of Reasons for Rejection Dated Feb. 18, 2011 From the Japanese Patent Office Re. Application No. 2007-503494 and Its Translation into English.
Request for Formal Examination Dated Feb. 24, 2011 From the ROSPATENT, Federal Government Institution, Federal Institute of Industrial Property of the Federal Service for Intellectual Property, Patents and Trademarks of the Russian Federation Re. Application No. 2010146714.
Office Action Dated Apr. 5, 2011 From the Israel Patent Office Re.: Application No. 156070 and Its Translation Into English.
Response Dated Mar. 10, 2011 to Notification of Reasons for Rejection of Dec. 24, 2010 From the Japanese Patent Office Re. Application No. 2007-503495.

Official Action Dated May 6, 2013 From the US Patent and Trademark Office Re. U.S. Appl. No. 11/886,248.
Requisition by the Examiner Dated May 28, 2013 From the Canadian Intellectual Property Office Re. Application No. 2,600,988.
Communication Relating to the Results of the Partial International Search Dated Jan. 12, 2009 From the International Searching Authority Re.: Application No. PCT/IL2007/000893.
Communication Under Rule 71(3) EPC Dated May 27, 2011 From the European Patent Office Re. Application No. 09735573.9.
Examination Report Dated Oct. 13, 2010 From the Instituto Mexicano de la Propriedad Industrial Re. Application No. MX/a/2007/011339.
Examination Report Dated Mar. 31, 2011 From the Instituto Mexicano de la Propriedad Industrial Re. Application No. MX/a/2007/011339.
International Search Report and the Written Opinion Dated May 9, 2011 From the International Searching Authority Re. Application No. PCT/IL2010/000985.
International Search Report Dated Oct. 24, 2008 From the International Searching Authority Re.: Application No. PCT/IL2008/000786.
Interview Summary Dated Feb. 9, 2011 From the US Patent and Trademark Office Re.: U.S. Appl. No. 10/593,367.
Letter After Telephone Conference Dated Jul. 5, 2010 From the International Searching Authority Re. Application No. PCT/IL2009/000443.
Notification Dated Dec. 17, 2008 From the Patent Office of the Russian Federation Re.: Application No. 2006136791 and Its Translation Into English.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Official Action Dated Sep. 5, 2008 From the US Patent and Trademark Office Re.: U.S. Appl. No. 10/557,865.
Official Action Dated May 31, 2011 From the US Patent and Trademark Office Re. U.S. Appl. No. 12/417,011.
Response Dated Jan. 12, 2011 to Examination Report of Oct. 13, 2010 From the Instituto Mexicano de la Propriedad Industrial Re. Application No. MX/a/2007/011339.
Response Dated Mar. 25, 2010 to Official Action of Feb. 19, 2010 From the US Patent and Trademark Office Re.: U.S. Appl. No. 10/593,367.
Translation of Office Action Dated Apr. 29, 2011 From the State Intellectual Property Office of the People's Republic of China Re.: Application No. 200680017262.2.
Translation of Office Action Dated Jan. 29, 2010 From the State Intellectual Property Office of the People's Republic of China Re.: Application No. 200680017262.2.
Written Opinion Dated Oct. 24, 2008 From the International Searching Authority Re.: Application No. PCT/IL2008/000786.
International Preliminary Report on Patentability Dated Jun. 7, 2012 From the International Bureau of WIPO Re. Application No. PCT/IL2010/000985.
Translation of Decision for Rejection Dated Jun. 9, 2011 From the Japanese Patent Office Re. Application No. 2007-503495.
Response Dated Jun. 1, 2011 to Notification of Reasons for Rejection of Mar. 18, 2011 From the Japanese Patent Office Re. Application No. 2006-531002.
Response Dated May 29, 2011 to Communication Pursuant to Article 94(3) EPC of Feb. 4, 2011 From the European Patent Office Re. Application No. 04734069.0.
Official Action Dated Jun. 21, 2011 From the US Patent and Trademark Office Re.: U.S. Appl. No. 10/593,367.
Response Dated Jun. 20, 2011 to Office Action of Dec. 21, 2010 From the State Intellectual Property Office of the People's Republic of China Re. Application No. 200780033622.2.
Translation of Office Action Dated Dec. 21, 2010 From the State Intellectual Property Office of the People's Republic of China Re. Application No. 200780033622.2.
Examination Report Dated May 30, 2012 From the Instituto Mexicano de la Propiedad Industrial Re. Application No. MX/a/2007/011339 and Its Translation Into English.

(56) References Cited

OTHER PUBLICATIONS

Response Dated Jun. 29, 2011 to Office Action of Apr. 29, 2011 From the State Intellectual Property Office of the People's Republic of China Re.: Application No. 200680017262.2.
Response Dated Jun. 5, 2011 to the Communication Pursuant to Article 94(3) EPC of Feb. 4, 2011 From the European Patent Office Re. Application No. 04734069.0.
Official Action Dated Jul. 23, 2012 From the US Patent and Trademark Office Re. U.S. Appl. No. 12/373,937.
Office Action Dated Jul. 24, 2011 From the Israel Patent Office Re. Application No. 176883 and Its Translation Into English.
Response Dated Aug. 11, 2011 to Examination Report of Mar. 31, 2011 From the Instituto Mexicano de la Propriedad Industrial Re. Application No. MX/a/2007/011339.
Examination Report Dated Feb. 16, 2012 From the Government of India, Patent Office, Intellectual Property Building Re. Application No. 3837/CHENP/2006.
Official Action Dated Mar. 12, 2013 From the US Patent and Trademark Office Re. U.S. Appl. No. 12/680,575.
Supplemental Notice of Allowability Dated Apr. 2, 2013 From the US Patent and Trademark Office Re. U.S. Appl. No. 12/373,937.
Translation of Office Action Dated Mar. 5, 2013 From the State Intellectual Property Office of the People's Republic of China Re. Application No. 200980123856.5.
Translation of Reasons for Rejection Dated Mar. 18, 2013 From the Japanese Patent Office Re. Application No. 2011-223943.
Official Action Dated Apr. 9, 2012 From the US Patent and Trademark Office Re. U.S. Appl. No. 12/417,011.
Request for Examination Dated Mar. 29, 2012 From the Federal Institute of Industrial and Intellectual Property, Patents and Trademarks, ROSPATENT, of the Russian Federation Re.: Application No. 2010100368 and Its Summary in English.
Requisition by the Examiner Dated May 22, 2012 From the Canadian Intellectual Property Office Re. Application No. 2,560,877.
Response Dated Aug. 7, 2011 to Office Action of Apr. 5, 2011 From the Israel Patent Office Re.: Application No. 156070.
Response Dated Aug. 10, 2011 to Official Action of May 31, 2011 From the US Patent and Trademark Office Re. U.S. Appl. No. 12/417,011.
Patent Examination Report Dated Aug. 9, 2012 From the Australian Government, IP Australia Re. Application No. 2007274574.
Requisition by the Examiner Dated Aug. 22, 2012 From the Canadian Intellectual Property Office Re. Application No. 2,600,988.
Requisition by the Examiner Dated Aug. 29, 2011 From the Canadian Intellectual Property Office Re. Application No. 2,560,877.
Official Action Dated Aug. 24, 2012 From the US Patent and Trademark Office Re. U.S. Appl. No. 11/886,248.
Official Action Dated Oct. 14, 2011 From the US Patent and Trademark Office Re. U.S. Appl. No. 12/417,011.
Restriction Official Action Dated Nov. 1, 2012 From the US Patent and Trademark Office Re. U.S. Appl. No. 12/680,575.
Communication Pursuant to Article 94(3) EPC Dated Nov. 3, 2011 From the European Patent Office Re. Application No. 07789949.0.
Response Dated Oct. 19, 2011 to Official Action of Jun. 21, 2011 From the US Patent and Trademark Office Re.: U.S. Appl. No. 10/593,367.
Response Dated Nov. 21, 2011 to Examiner's Report of Nov. 29, 2010 From the Australian Government, IP Australia Re. Application No. 2006224158.
Notice of Allowance Dated Nov. 14, 2011 From the US Patent and Trademark Office Re.: U.S. Appl. No. 10/593,367.
Examination Report Dated Oct. 13, 2011 From the Instituto Mexicano de la Propriedad Industrial Re. Application No. MX/a/2007/011339.
Translation of Office Action Dated Nov. 22, 2012 From the State intellectual Property Office of the People's Republic of China Re. Application No. 200780033622.2.
Translation of Search Report Dated Nov. 22, 2012 From the State Intellectual Property Office of the People's Republic of China Re. Application No. 200780033622.2.

Response Dated Oct. 11, 2011 to Decision for Rejection of Jun. 9, 2011 From the Japanese Patent Office Re. Application No. 2007-503495.
Response Dated Mar. 28, 2011 to Official Action of Dec. 28, 2010 From the US Patent and Trademark Office Re.: U.S. Appl. No. 10/593,367.
Translation of Notification of Reasons for Rejection Dated Mar. 18, 2011 From the Japanese Patent Office Re. Application No. 2006-531002.
Translation of Office Action Dated Feb. 22, 2012 From the State Intellectual Property Office of the People's Republic of China Re. Application No. 200780033622.2.
Request for Examination Dated Apr. 4, 2013 From the Federal Service for Intellectual Property, Federal State Budgetary Institution, Federal Institute of Industrial Property of the Russian Federation Re. Application No. 2010146714 and Its Summary in English.
Response Dated Jan. 17, 2011 to Examiner's Report of Dec. 15, 2010 From the Australian Government, IP Australia Re.: Application No. 2005221424.
Communication Pursuant to Rules 70(2) and 70a(2) EPC and Reference to Rule 39(1) EPC Dated Jan. 9, 2012 From the European Patent Office Re. Application No. 11179593.6.
Translation of Office Action Dated Aug. 22, 2013 From the State Intellectual Property Office of the People's Republic of China Re. Application No. 200780033622.2.
European Search Report and the European Search Opinion Dated Nov. 14, 2013 From the European Patent Office Re. Application No. 11188150.4.
Applicant-Initiated Interview Summary Dated Jun. 28, 2013 From the US Patent and Trademark Office Re. U.S. Appl. No. 12/680,575.
Official Action Dated Jul. 1, 2013 From the US Patent and Trademark Office Re. U.S. Appl. No. 12/663,714.
Applicant-Initiated Interview Summary Dated Aug. 9, 2013 From the US Patent and Trademark Office Re. U.S. Appl. No. 12/680,575.
Invitation Pursuant to Rule 62a(1) EPC Dated Aug. 8, 2013 From the European Patent Office Re. Application No. 06711327.4.
Communication Pursuant to Rules 70(2) and 70a(2) EPC Dated Nov. 8, 2013 From the European Patent Office Re. Application No. 06711327.4.
Notice of Allowance Dated Oct. 2, 2013 From the US Patent and Trademark Office Re. U.S. Appl. No. 12/417,011.
Notification of Reasons for Rejection Dated Oct. 4, 2013 From the Japanese Patent Office Re. Application No. 2011-223943 and Its Translation Into English.
Official Action Dated Sep. 24, 2013 From the US Patent and Trademark Office Re. U.S. Appl. No. 13/772,410.
Supplemental Notice of Allowability Dated Sep. 24, 2013 From the US Patent and Trademark Office Re. U.S. Appl. No. 11/886,248.
Supplementary European Search Report and the European Search Opinion Dated Oct. 21, 2013 From the European Patent Office Re. Application No. 06711327.4.
Translation of Office Action Dated May 6, 2013 From the State Intellectual Property Office of the People's Republic of China Re. Application No. 200780033622.2.
Communication Pursuant to Article 94(3) EPC Dated Nov. 29, 2013 From the European Patent Office Re. Application No. 08808093.2.
Office Action Dated Nov. 12, 2013 From the State Intellectual Property Office of the People's Republic of China Re. Application No. 200980123856.5 and Its Translation into English.
Communication Pursuant to Rules 70(2) and 70a(2) EPC and Reference to Rule 39(1) EPC Dated Jan. 2, 2014 From the European Patent Office Re. Application No. 11188150.4.
Office Action Dated Dec. 19, 2013 From the Israel Patent Office Re. Application No. 219989 and Its Translation Into English.
Office Action Dated Dec. 31, 2013 From the Israel Patent Office Re. Application No. 219988 and Its Translation Into English.
Office Action Dated Dec. 31, 2013 From the Israel Patent Office Re. Application No. 222951 and Its Translation Into English.

\* cited by examiner

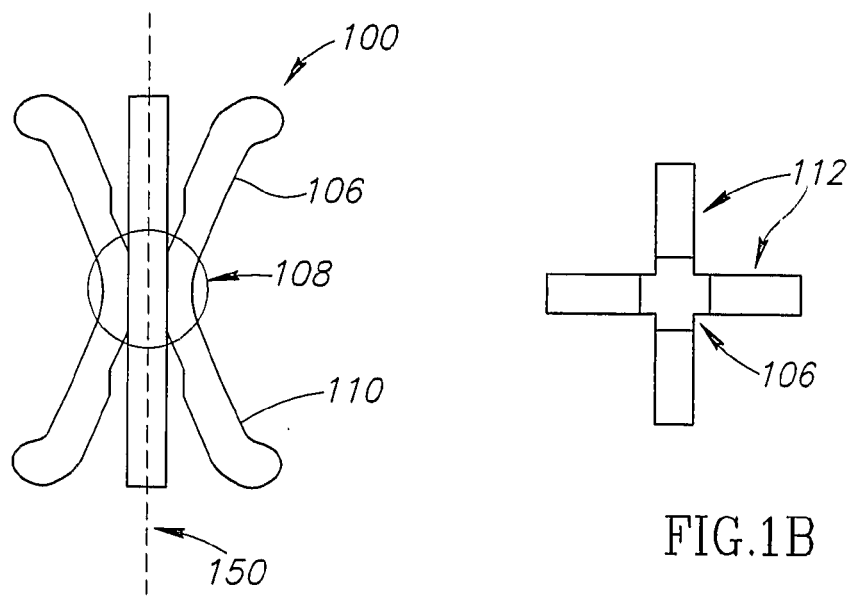
FIG.1A
FIG.1B
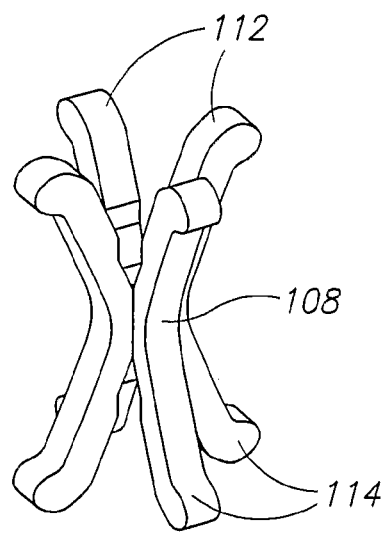
FIG.1C
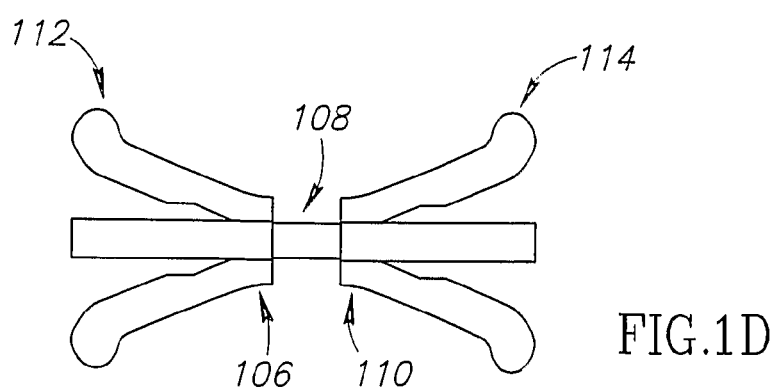
FIG.1D

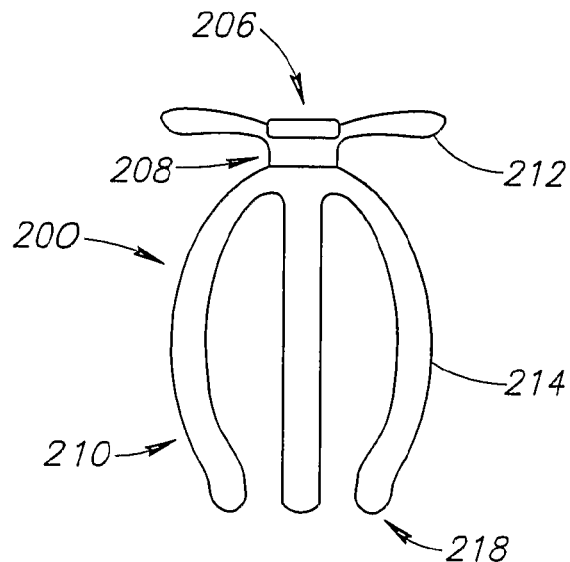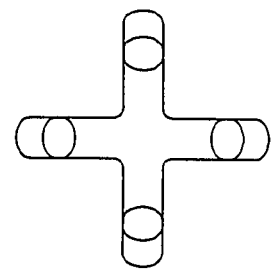
FIG.2A  FIG.2B
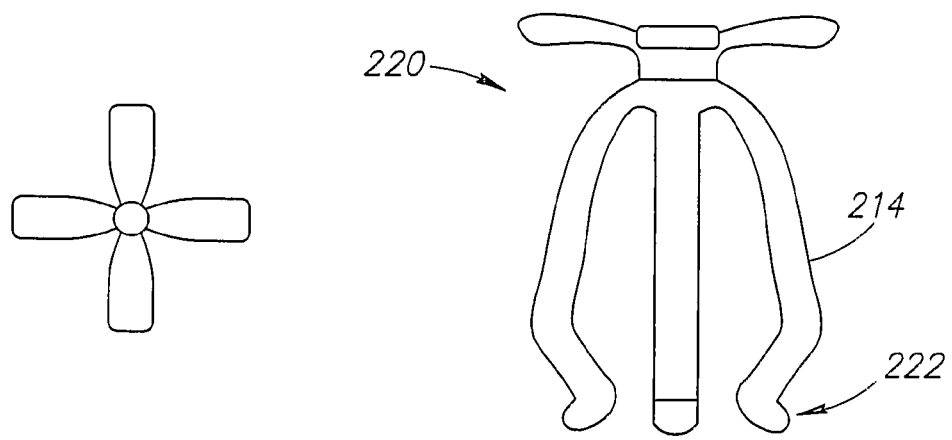
FIG.2C  FIG.2D

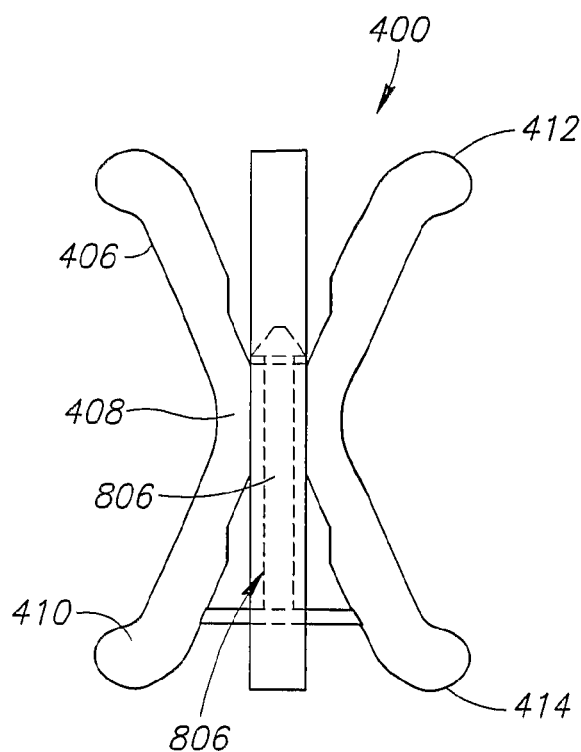
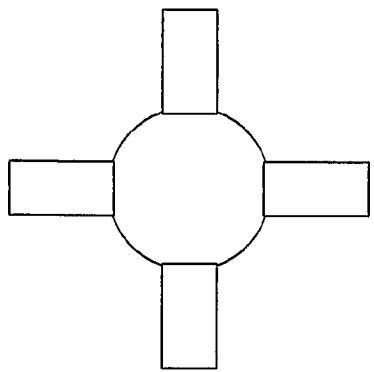
FIG.4A  FIG.4B
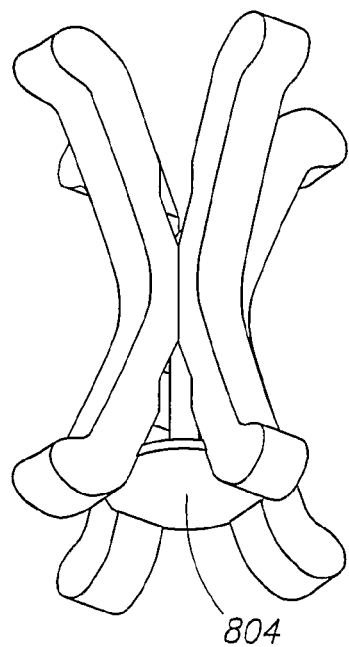
FIG.4C

APPARATUS FOR THE PREVENTION OF URINARY INCONTINENCE IN FEMALES

RELATED APPLICATIONS

The present application is a US National Phase of PCT Application No. PCT/IL2005/000304, filed on Mar. 17, 2005. This application is also a continuation-in-part of U.S. Ser. No. 10/557,865 which is a national phase of PCT Application No. PCT/IL2004/000433, filed on May 20, 2004 which claims priority from Israel Patent Application No. 156070 filed on May 22, 2003 and Israel Patent Application No. 157117, filed on Jul. 27, 2003, the disclosures of which are herein incorporated by reference. The present application also claims the benefit under 35 USC 119(e) of U.S. Provisional Application No. 60/553,964, filed on Mar. 18, 2004; U.S. Provisional Application No. 60/555,977, filed on Mar. 25, 2004; U.S. Provisional Application No. 60/570,469, filed on May 13, 2004; U.S. Provisional Application No. 60/570,535, filed on May 13, 2004; U.S. Provisional Application No. 60/598,835, filed on Aug. 5, 2004 and U.S. Provisional Application No. 60/602,636, filed on Aug. 19, 2004, the disclosures of which are herein incorporated by reference.

FIELD OF INVENTION

The present invention relates generally to urinary incontinence in females, for example by providing devices for the prevention of female incontinence.

BACKGROUND OF THE INVENTION

Urinary incontinence is a widespread problem among females. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. While many different factors may contribute to the development of stress incontinence, it is most prevalent among women ages 35-65 and those who have had multiple vaginal deliveries. Stress incontinence is both aggravating and unpleasant for women, and it can also be embarrassing. Many women wear sanitary pads or diapers in order to deal with incontinence, though this is not a real solution to the problem and it can be very inconvenient and unreliable. Surgical treatment may involve securing the paraurethal tissues to the periosteum of the pubic bone or the rectus facia in order to elevate the bladder neck above the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath the mid-urethra, creating a hammock on which the urethra may kink during a rise in intra-abdominal pressure. However, surgery is only suitable for severe cases, and the majority of women experiencing incontinence do not need surgical solutions.

One modality of non-surgical treatment involves the use of devices that are inserted into the vagina, either by a medical practitioner or by the woman herself. Most devices are designed to apply pressure against the bladder neck so as to inhibit or completely block the flow of urine through the urethra. A variety of such devices are known in the art. For example, refer to U.S. Patent Application No. 2002/0183711 to Moser, entitled, "Urinary Incontinence Device"; U.S. Pat. No. 6,739,340 to Jensen, et al., entitled, "Device for prevention of involuntary urination"; U.S. Pat. No. 6,679,831 to Zunker, et al., entitled, "Resilient incontinence insert and a method of making the same"; U.S. Pat. No. 6,460,542 to James, entitled, "Female incontinence control device"; U.S. Pat. No. 6,413,206 to Biswas, entitled, "Intra-vaginal device"; U.S. Pat. No. 5,785,640 to Kresch, entitled "Method for Treating Female Incontinence"; U.S. Pat. No. 5,771,899 to Martelly, et al., entitled, "Pessary"; U.S. Pat. No. 5,618,256 to Reimer, entitled, "Device for Arrangement in the Vagina for Prevention of Involuntary Urination with Females and an Applicator for use in Insertion of the Device"; U.S. Pat. No. 5,417,226 to Juma, entitled, "Female Anti-Incontinence Device"; U.S. Pat. No. 5,386,836 to Biswas, entitled, "Urinary Incontinence Device"; U.S. Pat. No. 5,007,894 to Enhorning, entitled, "Female Incontinence Device"; and U.S. Pat. No. 4,920,986 to Biswas, entitled, "Urinary Incontinence Device", the disclosures of which are herein incorporated by reference.

One problem with many of the above listed devices is that they completely block the urethra and thus they need to be removed or collapsed in order to allow the woman to urinate. To overcome this drawback, vaginal devices have been developed having specialized shapes that do not completely block the bladder neck but these devices tend to be large, uncomfortable, and intrusive. They also tend to cause irritation or soreness to the vagina.

Another common shortcoming is that most devices known in the art also tend to be difficult or painful to insert and/or remove. In order to correctly inhibit urine flow, the device needs to be properly positioned in the vaginal canal. As a result, a doctor may be required to properly position the device. In most cases, the device is adapted for remaining in the vagina for a prolonged period of time (due to the time and expense of requiring a trained medical professional to insert the device). However, when positioned in the vagina for an extended period of the time, the device may cause vaginal infections, necrosis, or bleeding.

SUMMARY OF THE INVENTION

An aspect of some embodiments of the invention relates to a device for treating feminine incontinence which is comprised of at least a node. Optionally, the length of the node is only 30% or less of the length of the entire device. In some embodiments of the invention, the device further comprises an anchor and a support. In some embodiments of the invention, the node construction allows for greater flexibility control of the device for improved function. Optionally, a flexible neck portion is located at the node of the device. Flexibility, especially at the central core body, enhances comfort to the wearer. In some embodiments of the invention, a device for treating feminine incontinence is provided which is disposable. Optionally, the device is of unitary body construction. Optionally, the device is constructed of a single material. Optionally, the device is manufactured in varying sizes. For example, in some embodiments of the invention devices are provided which are between 30 mm and 50 mm in total length. Optionally, the devices are larger or smaller depending on the needs of the individual user. In some embodiments of the invention, the device is inserted using an applicator.

In an exemplary embodiment of the invention, the device has anchor and support portions provided with arms. Optionally, the shape and number of arms are variable. Optionally, there are four support and/or anchor arms. Optionally, there are more or less than four arms. Optionally, the arms are not the same shape. Optionally, the arms are provided with varying degrees of compliance, rigidity and resiliency. Optionally, the arms are provided with soft tips or pads. In some embodiments of the invention, the angle of the arms with respect to the central axis of the device and/or each other can be changed. Optionally, the support arms are curved. Optionally, the anchor arms radiate substantially perpendicular from the node. In some embodiments of the invention, the size and shape of the support arms are not related to the size and shape of the anchor arms. Optionally, the arms are cantilevered.

In an exemplary embodiment of the invention, the device includes an additional structure which exerts direct pressure to the urethra for enhanced incontinence treatment. Optionally, the device with additional structure is used during strenuous physical activity. In some embodiments of the invention, direct pressure to the urethra is applied by a ring strut which connect the arms of the support section. Optionally, the strut is comprised of straight segments. Optionally, the strut is comprised of inwardly arcing segments.

An aspect of some embodiments of the invention relates to a device for treating feminine incontinence which is provided with an adjustable size of urethral support. Optionally, the support size is adjustable mechanically, for example by using an extending insert. Optionally, portions of the device are cantilevered. Optionally, the extending insert is interchangeable with other extending inserts in order to modify the support dimensions. Variable shape and size allow for a better fit to the wearer and in some cases deliver more effective therapy.

An aspect of some embodiments of the invention relates to a device for treating feminine incontinence which includes a device displacer, such as a string. In an exemplary embodiment of the invention, upon application of removal force on the string, the arms of the device collapse towards the node, reducing the device's profile and allowing for easier and less pain inducing removal. Optionally, the string is attached directly to the support arms, whereupon application of force on the string, at least the support arms collapse for easier removal. Optionally, the string is attached to the sling-like device or cover, whereupon application of force on the string, the sling-like device exerts force on the arms and causes them to collapse for easier removal. Optionally, the device is removed without the patient having to touch herself.

There is thus provided an apparatus for treating urinary incontinence, comprising: a node; a support section adapted for providing urethral support attached to said node; and, an anchoring section adapted for resisting movement of said apparatus attached to said node; wherein said node is no longer than 30% of the entire length of said apparatus comprising said node, support section and said anchoring section together. Optionally, the node is no longer than 20% of the entire length of said apparatus for treating urinary incontinence. Optionally, the node is no longer than 15% of the entire length of said apparatus for treating urinary incontinence. In some embodiments of the invention, the support section is provided with at least 2 supporting arms. In some embodiments of the invention, the anchoring section is provided with at least 2 anchoring arms. Optionally, the apparatus further comprises a cover. Optionally, the cover substantially encapsulates said node, support section and said anchoring section. In some embodiments of the invention, the support section and said anchoring section are flexible. Optionally, the node is flexible. In some embodiments of the invention, the apparatus further comprises a device displacer. Optionally, the device displacer is attached to said support section. In some embodiments of the invention, the apparatus further comprises support struts interlinking said supporting arms. In some embodiments of the invention, the apparatus further comprises an applicator adapted to insert said apparatus into a vagina.

There is thus provided an apparatus for treating urinary incontinence, comprising: a support section adapted for providing urethral support; and an extending insert adapted to adjust the diameter of said support section. In some embodiments of the invention, the apparatus further comprises a node and an anchoring section adapted for resisting movement of said apparatus. In some embodiments of the invention, the apparatus further comprises a cover. Optionally, said cover substantially encapsulates said node, support section, said anchoring section and extending insert. In some embodiments of the invention, the apparatus further comprises a device displacer. Optionally, a device displacer is attached to said support section. In some embodiments of the invention, the apparatus further comprises an applicator adapted to insert said apparatus into a vagina.

There is thus provided an apparatus for treating urinary incontinence, comprising: a body adapted for treating incontinence when inserted in a vagina; and, a device displacer for providing movement to said apparatus. Optionally, said device displacer is a string. In an exemplary embodiment of the invention, said apparatus is flexible and distorted by said string.

There is thus provided a method of using an apparatus for the treatment of urinary incontinence, comprising: inserting said incontinence treating apparatus; and, deploying said incontinence treating apparatus in a position to render mid-urethral support. Optionally, inserting is facilitated by an applicator. In some embodiments of the invention, the method further comprises removing said apparatus. Optionally, removing is facilitated by a device displacer.

There is thus provided an apparatus for inserting a vaginal device, comprising: an enclosure for containing said vaginal device; and a stopper, wherein said stopper prevents over insertion. Optionally, said stopper is located on said enclosure in a position such that upon insertion of said apparatus into said vagina up to said stopper, said vaginal device will be in appropriate position within said vagina for deployment. In an exemplary embodiment of the invention, said stopper is adjustably located on said enclosure.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIG. 1A is a profile view of the internal support structure in an exemplary embodiment of the invention;

FIG. 1B is a top view of the internal support structure in an exemplary embodiment of the invention;

FIG. 1C is a perspective view of the internal support structure in an exemplary embodiment of the invention;

FIG. 1D is a profile view of the internal support structure with an optional narrowed, flexible neck in an exemplary embodiment of the invention;

FIG. 2A is a profile view of an optional internal support structure in an exemplary embodiment of the invention;

FIG. 2B is a top view of an optional internal support structure in an exemplary embodiment of the invention;

FIG. 2C is a bottom view of an optional support structure in an exemplary embodiment of the invention;

FIG. 2D is a profile view of an optional internal support structure with outward projecting arm tips in an exemplary embodiment of the invention;

FIG. 4A is a profile view of an expandable internal support structure in an exemplary embodiment of the invention;

FIG. 4B is a top view of an expandable internal support structure in an exemplary embodiment of the invention;

FIG. 4C is a perspective view of an expandable internal support structure in an exemplary embodiment of the invention;

FIG. 5A is a profile view of the extending insert in an exemplary embodiment of the invention;

DETAILED DESCRIPTION OF EXEMPLARY EMBODIMENTS

Introduction

Figure 3A:
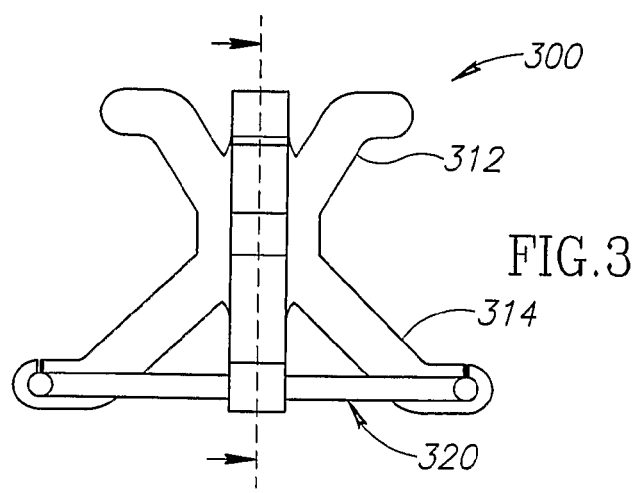
FIG. 3A is a profile view of an optional internal support structure with urethral support ring in an exemplary embodiment of the invention.
Figure 3B:
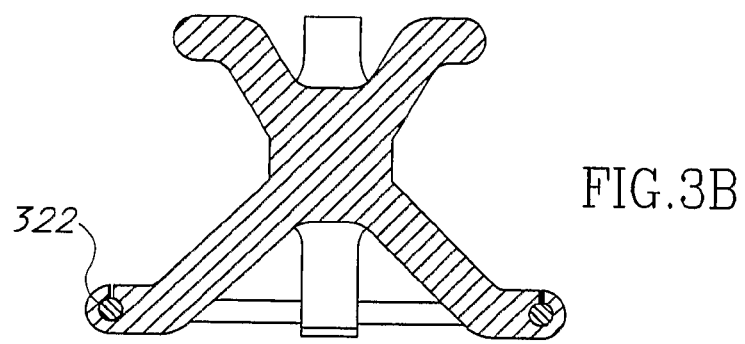
FIG. 3B is a cutaway view of an optional internal support structure with urethral support ring in an exemplary embodiment of the invention.
Figure 3C:
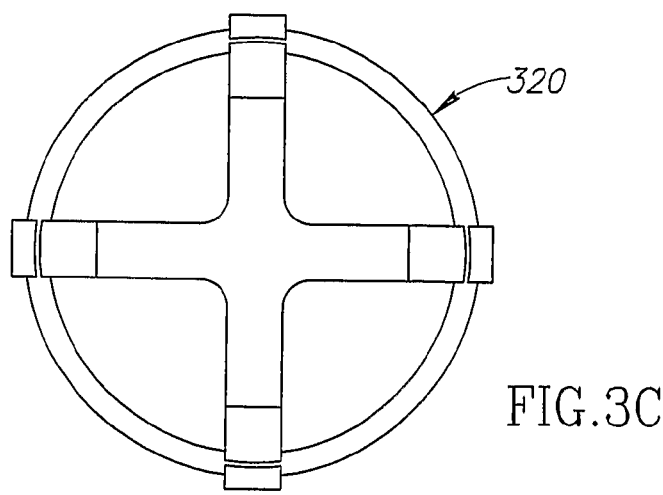
FIG. 3C is a top view of an optional internal support structure with urethral support ring in an exemplary embodiment of the invention.
Figure 3D:
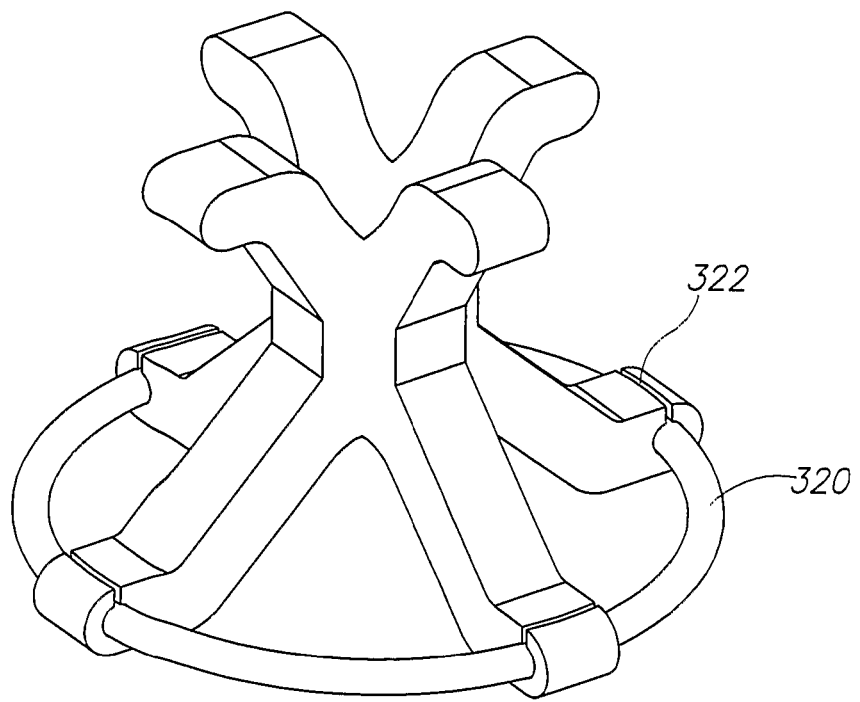
FIG. 3D is a perspective view of an optional internal support structure with support ring in an exemplary embodiment of the invention.

The present invention provides a device, and variations of the device, for the treatment of urinary incontinence females. The device of the present invention is adapted to be disposable, worn only for a short period of time and then discarded and replaced with a new device (if needed). Alternatively, the device is recycled for use by sterilizing it in between uses. The device of the present invention is simple and easy to use, and is optionally inserted effortlessly in the same user-friendly and familiar manner that a tampon is inserted into the vagina during menstruation. As opposed to large and intrusive devices of the prior art, the device of the present invention is comfortable, and, once inserted, the woman need not think about it again until it is removed. When involuntary urination occurs, it often happens because of a rise in pressure in the bladder for which there is no compensating counter-pressure from the bladder neck or urethra. This is usually the result of the abnormal descent of the bladder neck and the urethra into a low position, away from the intra-abdominal pressure system. Known as "hypermobility", this is the result of some injury to the support mechanism which normally keeps the urethra and the bladder neck in a raised position, along the backside of the pubic bone. The lowering of the bladder neck and the urethra that occur, for example, when a woman coughs, sneezes, or laughs, causing involuntary leakage of urine.

A Device for Treating Incontinence

Referring to FIG. 1A, a profile view of an exemplary embodiment of the incontinence device 100 is shown. For ease of description, the device 100 is arranged around a central axis 150 and divided into three parts. A top section 106 is provided which serves as the "anchoring" element, for stabilizing the device within the vagina. There are two types of anchoring, axial anchoring which acts in the direction along the central axis of the vagina, and radial anchoring which acts side-to-side or substantially perpendicular to the central axis of the vagina. A bottom section 110 is provided which serves as the "supporting" element, for generating urethral support. In some embodiments of the invention, support is generated at a mid-urethral location. In some embodiments of the invention, the bottom supporting section 110 provides at least one form of anchoring to help anchor device 100 in position. In some embodiments of the invention, the entire length of device 100 is between 30 mm and 50 mm. optionally, device 100 is larger or smaller depending on the individual needs of the patient.

Also, an intermediate section 108 is provided which acts as a "node" and which connects anchoring 106 and supporting 110 elements. The node 108 of this and many other devices described herein has a length which is only a small portion of the overall length of the device, in some embodiments of the invention. In some embodiments of the invention, the length of the node is less than 15% of the entire length of the device. In some embodiments of the invention, the length of the node is less than 20% of the entire length of the device. In other embodiments of the invention, the length of the node is less than 30% the entire length of the device. In some embodiments of the invention, a node which is short relative to the entire length of the device allows for more flexibility in varying the stiffness, the comfort, and the size of device 100. Optionally, the node is not provided with one axis longer than the other, the axes are equal in length (e.g. a sphere or a cube). In arm exemplary embodiment of the invention, a small node in relation to the overall length of the device allows for greater control over the behavior of the anchoring and support arms, described below.

Figure 9A:
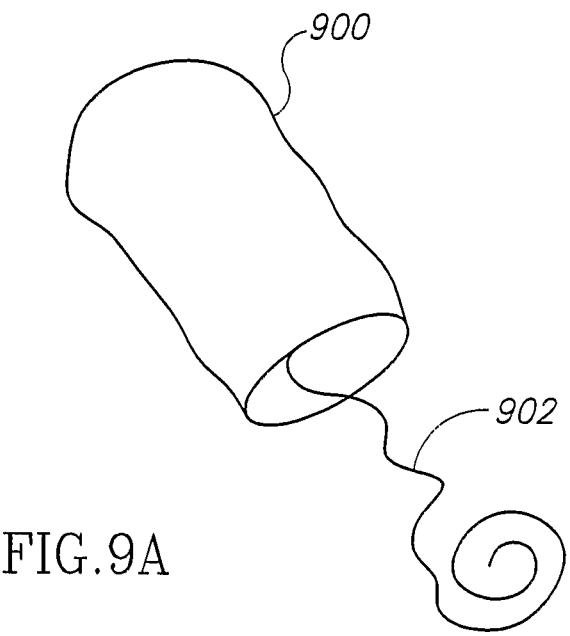
FIG. 9A is an illustration of an optional cover in an exemplary embodiment of the invention.

The elements of the device 100 function as an internal support structure for a cover, depicted in FIGS. 9A and B, in some embodiments of the invention. It should also be noted that for certain women, the described devices herein can also be used as a treatment for prolapse.

In an exemplary embodiment, the anchoring element 106 and the supporting element 110 have four (4) arms 112 and 114, respectively. In an exemplary embodiment of the invention, four arms are provided to each section in which two generally exert pressure towards the bladder, and two generally exert pressure towards the vaginal floor adjacent the bowels. The two support arms which exert pressure towards the bladder fit within natural slots on either side of the urethra in some embodiments of the intention. Optionally, the anchoring and supporting elements are provided with more or less arms. For example, the anchoring element could have more arms if there is concern about unwanted movement of device 100. In other embodiments of the invention, the arms are provided at varied angles with respect to the node 108 and/or each other. Optionally the arms 112 and 114 are flexible or rigid and are constructed of a biocompatible material. In an exemplary embodiment of the invention, the anchoring element does not apply significant pressure to the wearer's vagina and/or urethra, thereby enhancing comfort. In some embodiments of the invention, other structure is provided instead of arms which is capable of supporting the urethra, in the case of the support section, or preventing the device from unintentionally moving, in the case of the anchor section. For example, at least one cone, protrusions, and/or extensions attached to the node could be used for anchoring and support.

The anchoring arms of the device prevent the device from moving unintentionally out of position. In an exemplary embodiment of the invention, the arms are flexible. This flexibility enhances the anchoring arms' ability to prevent motion of the device further into the vagina. As force strives to exert itself on the device, and move it into the vagina, the flexible anchoring arms tend to spread apart. This spreading action of the anchoring arms increases the friction between the device and the vaginal wall, prevent movement. While the arms are flexible, it should be noted that they are rigid enough to prevent unwanted motion of the device towards the entrance of the vagina. Optionally, the arms are rigid but the node is flexible, the node thus providing flexible anchoring and support. Movement towards the vaginal opening is resisted by the arms which position themselves just on the posterior side, in relation to the vaginal opening, of a hump located in the vagina. These features work independently from and in conjunction with the tenting behavior of the vaginal walls described above, which also helps to maintain the device in place.

An additional feature of the anchoring arms of the device 100 is that they operate remotely from the support arms. This reduces the amount of pressure applied to the urethra by the device. Alternatively or additionally, the remote position of the anchoring arms in relation to the support element is calculated so that the anchoring arms can position themselves just on the posterior side, in relation to the vaginal opening, of a hump located in the vagina while the supporting arms provide mid-urethral support. Such a configuration increases comfort to the wearer, prevents unnecessary damage to the tissues adjacent to the device, increases the anchoring function of the device, and in some embodiments of the invention allows the wearer to void voluntarily without having to remove the device to urinate.

FIGS. 1B and 1C assist with illustrating the configuration of the device 100, and more specifically the arms 112 and 114, in an exemplary embodiment of the invention. The arms 112 of the anchoring element 106 force the device 100 to remain in situ within the vagina, unable to substantially move inwards or outwards, or to rotate. One reason this occurs is as a result of the special tendency of vaginal walls to collapse and form an occluded lumen. The arms of the device cause "tenting" of the walls on top of them with resultant sagging of the walls around the node 108, thereby stabilizing the device 100. The arms 114 of the supporting element 110 cause elevation of the tissues around mid-urethra, acting as a hammock. This hammock supports mid-urethra in a tension free manner, much like the TVT operation. In a woman who leaks urine during a stressful event (when abdominal pressure rises during coughing, sneezing, etc.), the urethra sags down but meets the hammock in its mid part. The meeting of the urethra and the hammock causes an elevation (sort of like a kinking of the urethra) of the intra-urethral pressure with resultant urinary continence. In some embodiments of the invention the radiating support arms 114 of device 100 create an overall device diameter of 25 mm to 50 mm within the vaginal cavity. Optionally, the diameter is larger or smaller depending on the individual needs of the patient.

In an exemplary embodiment of the invention, the anchor element arms 112 resist motion of the device towards the uterus because the arms increase their angle to the node 108. This effective increase in radius operates to counteract the motion of the device further into the vagina. In some embodiments of the invention, anchor element arms 112 are provided with a large angle to the node to enhance this anchoring effect. It should be noted that this enhanced anchoring effect is observed only up until a maximum angle.

FIG. 1D illustrates an embodiment of the invention in which the node 118 is narrowed. A narrowed node 118 increases the flexibility and the possible ranges of movement for the overall device 100 in some embodiments of the invention. Optionally, devices such as wires and/or springs are embedded in the neck in order to enhance flexibility for device 100. This additional flexibility can enhance the comfort of the woman while wearing the device 100. Any of the embodiments described herein are optionally utilized in conjunction with a narrowed node 118.

An Optional Substantially Perpendicular Anchor Arm Embodiment

Referring now to FIG. 2A, an additional embodiment of a device 200 is shown for battling feminine urinary incontinence. This embodiment is comprised of an anchor element 206, a support element 210 and a node 208. In this embodiment of the invention, the anchor element is provided with arms 212 which radiate substantially perpendicular to the node 208. This anchor element arm configuration is particularly useful for preventing inadvertent movement of the incontinence device towards the vaginal opening, although motion in either direction is resisted. As can be seen from FIG. 1A, the support element arms 214 are shaped such that they bend towards the central axis of the device 200, and the tips 218 of the arms do not substantially extend outwards away from the central axis of the device. This is in contrast to the embodiment 220 shown in FIG. 2D, wherein the tips 222 of the arms 214 extend away from the central axis of the device 200 significantly. In addition, the inward directed arm tips enhance the comfort of the wearer and in some embodiments of the invention facilitate device 200 removal, as their shape provides tips which do not jut into the vaginal wall. This embodiment functions in a similar manner to the device 100 of FIG. 1A.

The device 220 illustrated in FIG. 2D constitutes an alternate exemplary embodiment of the urinary incontinence device. As described above, the arm tips 222 extend radically away from the central axis of the device 220. This embodiment provides an elongated section wherein the urethra is supported. It should be noted that any of the shapes and sizes of the arms described in this application are interchangeable depending on the needs of the individual woman.

An Incontinence Device Adapted to Provide Supplemental Support

Not all women, and not all activity, can be treated with exactly the same devices when it comes to incontinence. For example, FIGS. 3A-D illustrate a device 300 which is adapted to directly compress the urethra during strenuous physical activity. Optionally, this embodiment is used for treatment of women who have relatively severe incontinence where the other embodiments described herein are ineffective. In an exemplary embodiment of the invention, this device 300 is provided with an anchor element, a support element and a node. Optionally, the device 300 is provided with anchor element arms 312 and support element arms 314.

In addition to the above, an additional support 320 is provided which is attached to the support element arms 314. Dependent on the level of external under-urethral pressure exerted by the additional support 320, there is optionally a full or partial occlusion of the urethra for a limited period of time. Attachment of the additional support 320 to the device 300 may be accomplished by using a notch 322 or by any other means of connection known in the art.

While the Figs. depict a generally circular additional support 320, it should be noted that any shape which can provide additional support to the urethra is optionally utilized. For example, the curvature of the additional support 320 segments can be biased inward towards the central axis (creating a plus sign shaped support) or the additional support 320 can consist of substantially straight segments (creating a box shape). Different shapes are optionally utilized depending on the needs of the individual wearer. Additionally or alternatively, the additional support 320 is of constant diameter at its entire length, or different diameters and widths.

Variable Geometry Incontinence Device

As mentioned previously, not all women can be treated with the same device. While the same basic anatomical features are generally present in every woman, the size of these features and their relationship to each other can vary slightly. Because of this, it can be difficult to provide a "one size fits all" type of device. The device depicted in FIG. 1 addresses this problem by providing a flexible device which is capable of adapting itself to multiple geometries. While it is possible that some women cannot use the device of FIG. 1, its features certainly reduce the number of sizes that need to be supplied. One optional way to solve this problem is illustrated in FIGS. 4A-C. The device 400 illustrated optionally consists of the same basic elements as some of the other embodiments (i.e. an anchoring element 406, a support element 410 and a node 408), however there are some modifications which allow for a variable geometry of the device 400. It can be seen from FIG. 4A that a device 400 is provided in which the geometry of the support element arms 414 can be adjusted, depending on the particular needs of the patient.

Figures 8A, 8B:
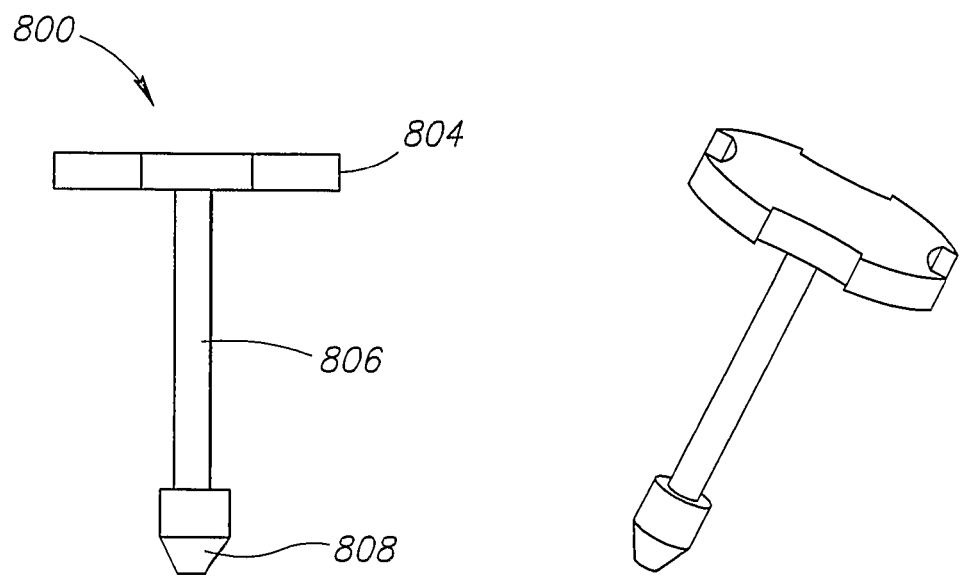
FIG. 8B is a perspective view of the extending insert in an exemplary embodiment of the invention.
Figure 8C:
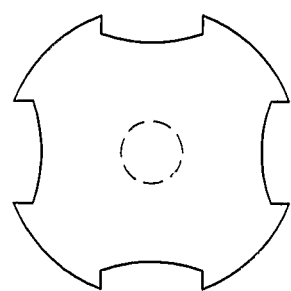
FIG. 8C is a top view of the extending insert in an exemplary embodiment of the invention.

An extending insert 800, depicted in FIGS. 8A-C, is positioned within the area proscribed by the support element arms 414. A shaft portion 806 of the extending insert 800 penetrates into a preformed tunnel within the device 400 along the central axis. The extending insert is provided with the ability to transit along the central axis of the device 400 towards the anchoring element 406. However, in an exemplary embodiment of the invention, the extending insert 800 is only capable of transit towards the anchoring element 406, not away from the anchoring element 406. Optionally, a device is provided which comprises two extending inserts on each side of the central axis of the node. Such an embodiment would allow for variable geometry control of the anchor element arms 412 and the support element arms 414.

Figure 5A:
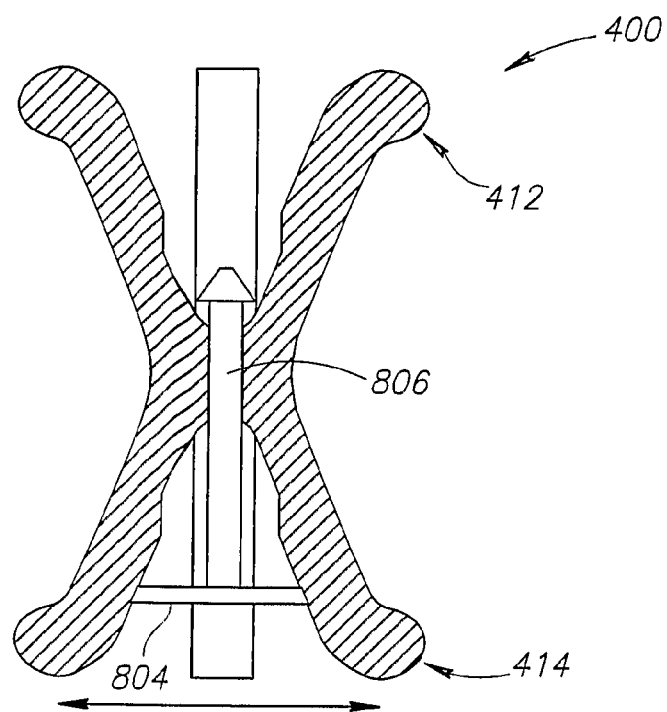
FIG. 5A is cutaway view of an expandable internal structure in a retracted configuration in an exemplary embodiment of the invention.
Figure 5B:
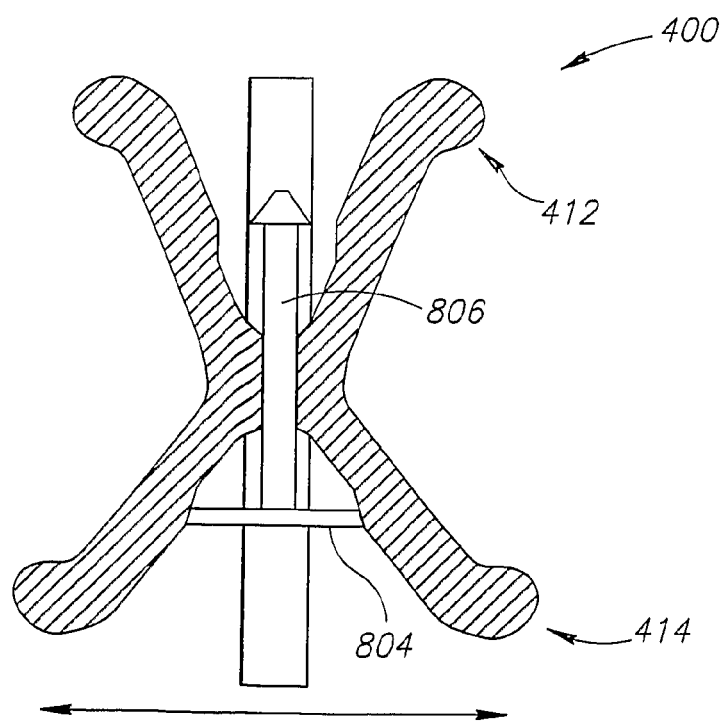
FIG. 5B is cutaway view of an expandable internal structure in an expanded configuration in an exemplary embodiment of the invention.

Referring now to FIG. 5A, a device 400 for treating incontinence with variable geometry is shown. The configuration of FIG. 5A illustrates the device 400 in its base state, without geometry modification by the extending insert 800. FIG. 5B, however, demonstrates how the extending insert 800 interacts with the device 400 to change the angle of the support element arms 414 with respect to the central axis of the device 400. It can be seen that as the extending insert 800 moves through the central axis of the device 400 towards the anchoring element 406, the support element arms 414 assume a wider angle to the central axis.

In an exemplary embodiment of the invention, the extending insert also provides an additional utility to the device 400. It also serves as a supplemental support element for the arms 414, mainly when a larger diameter is needed, to negate the counteracting forces from the vaginal walls.

Figure 6A:
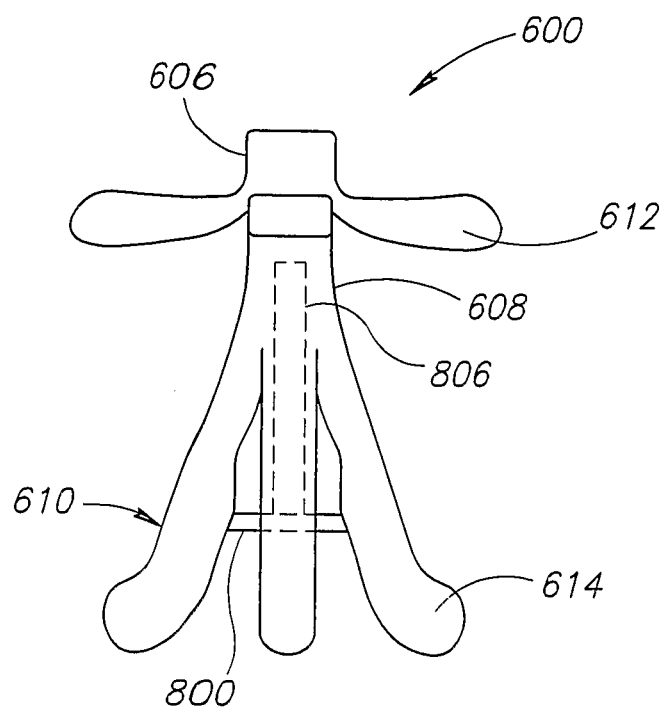
FIG. 6A is a profile view of an optional, expandable internal support structure in an exemplary embodiment of the invention.
Figure 6B:
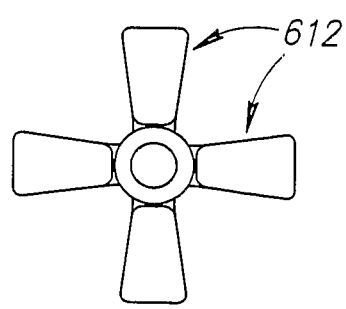
FIG. 6B is a top view of an optional, expandable internal support structure in an exemplary embodiment of the invention.
Figure 6C:
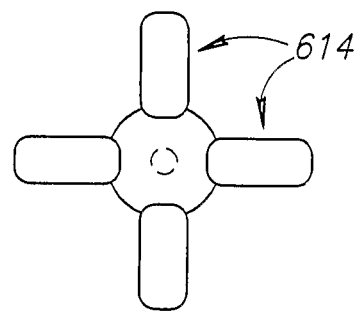
FIG. 6C is a bottom view of an optional, expandable internal support structure in an exemplary embodiment of the invention.

An Embodiment of a Variable Geometry Incontinence Device With Perpendicular Anchor Arms FIGS. 6A-C also illustrate an exemplary embodiment of the invention 600 in which the geometry is variable based on the position of an extending insert 800. The operation for variable motion is essentially the same as the embodiment depicted in FIGS. 4A-C, however, it is noted that the anchoring element arms 612 are of slightly different configuration. This type of arm configuration (i.e. extending substantially perpendicular to the central axis of the device 600) function similarly to the anchor element arms 212 depicted in FIGS. 2A-D. It should be understood that the embodiments depicted in the Figures are by way of example only, and that any of the variable geometry incontinence devices described or suggested herein can be used with an extending insert without regard to the size of the device, the number of the arms, the configuration of the arms, and/or the shape of the arms.

Figure 7A:
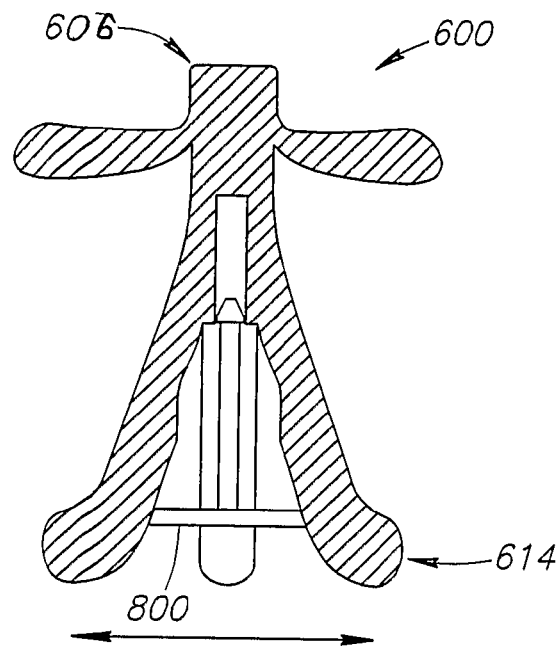
FIG. 7A is a cutaway view of an optional, expandable internal structure in a retracted configuration in an exemplary embodiment of the invention.
Figure 7B:
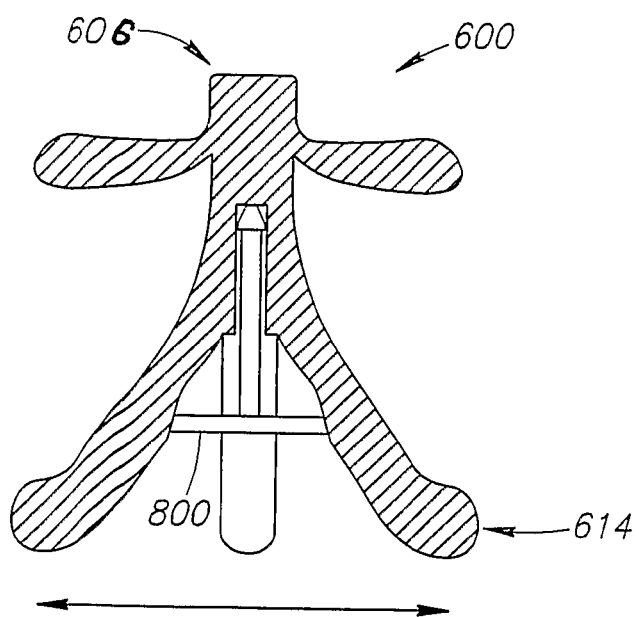
FIG. 7B is cutaway view of an optional, expandable internal structure in an expanded configuration in an exemplary embodiment of the invention.

Turning now to FIGS. 7A and B, the multiple geometry nature of the device 600 is shown. The configuration of FIG. 7A illustrates the device 600 in its base state, without geometry modification by the extending insert 800. FIG. 7B, however, demonstrates how the extending insert 800 interacts with the device 600 to change the angle of the support element arms 614, located on support element 610, with respect to the central axis and node 608 of the device 600. It can be seen that as the extending insert 800 moves through the central axis of the device 600 towards the anchoring element 606, the support element arms 614 assume a wider angle to the central axis.

FIGS. 8A-C show the extending insert 800 of an exemplary embodiment in greater detail. In this exemplary embodiment of the invention, the three basic components of the extending insert 800 are the head 804, the shaft 806 and the tip 808. In operation, the shaft 806 of the extending insert 800 is pushed into a tunnel located along the central axis of any of the variable geometry devices described herein. In an exemplary embodiment of the invention, the tip 808 is sized to be slightly larger than the diameter of the central axis tunnel. Furthermore, the tip 808 is shaped to facilitate insertion into the tunnel but to counter removal from the tunnel. Optionally, the extendible insert is maintained in the central tunnel by placing a series of protrusions along the inner circumference of the tunnel, which allow passage of the arrow shaped tip 808 when moving towards the anchor element, but which prevent passage of the wider tip 808 portion of the insert 800 back towards the support element. Optionally, various sized extendible inserts are provided which are interchangeable and which are chosen depending on the requirements for degree of angle in relation to the central axis. In an exemplary embodiment of the invention, an extendible insert is provided which positions different arms at different angles with respect to the central axis of an incontinence device. Optionally, some arms are not affected by the extendible insert. Optionally, the extendable insert is rotatable. Optionally, the head 804 of the extending insert 800 is constructed of a flexible material which allows it to be more easily inserted into an applicator 1100, the applicator depicted in FIG. 11.

Cover

Figure 9B:
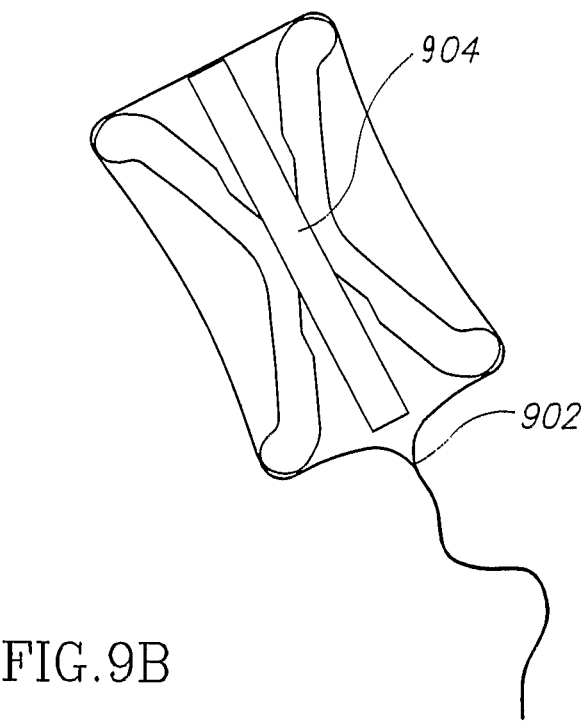
FIG. 9B is a cutaway showing an optional internal support structure within the cover in an exemplary embodiment of the invention.

FIG. 9A shows an incontinence device being used in conjunction with a cover 900. In an exemplary embodiment of the invention, the cover 900 is made of a flexible, smooth mesh material. Optionally, the cover 900 is designed as small sack which encapsulates the device 904, which acts as an internal support structure, shown in FIG. 9B. Use of the cover 900 can potentially provide one or more benefits in using the device. For example, the cover reduces friction between the applicator and the device upon insertion. In addition, the cover reduces friction between the vagina and the device during insertion. In some embodiments of the invention, the mesh of the cover 900, being stretched between the arms of the device, serves as a sling-like support for the urethra. In a woman who leaks urine during a stressful event (when abdominal pressure rises during coughing, sneezing, etc.), the urethra sags down but meets the cover 900 in its mid part. This causes an elevation of the intra urethral pressure with resultant urinary continence. In an exemplary embodiment of the invention, the device does not put pressure against the urethra or the bladder neck, but only provides support when there is a rise in abdominal pressure, as described above. Optionally, the device applies direct pressure to the urethra and/or bladder neck. In some embodiments of the invention, the cover 900 is disposable. Optionally, the cover is sterilized between uses and is reusable. Optionally, the cover is decorated.

In some embodiments of the invention, the cover 900 assists with removal of the device from the vagina. First, the cover 900 reduces friction between the incontinence device and the vaginal wall. Second, the cover 900 is optionally provided with a device displacer, such as a string 902. In an exemplary embodiment of the invention, the string 902 is attached to the cover 900. Optionally, the cover 900 and the string 902 are constructed of the same unitary piece of material. The string 902 assists with the removal of the device in a number of ways. Pulling the string 902 causes tightening of the cover 900. Tightening of the cover 900 causes the straightening of the vaginal walls. The straightening of the vaginal walls reduces the tent-like effect described above and relieves tension applied to the device, allowing for an easy and smooth removal of the device from the vagina. In addition, pulling on the string 902 causes the arms to fold slightly towards the central axis, thereby reducing its size and allowing for an easy and smooth removal of the device from the vagina. In an exemplary embodiment of the invention, the device can be "walked" out of the vagina by pulling on string 902 causing the support arms to move towards the vaginal opening (and thereby pulling the anchor section along), releasing the string suddenly, and then repeating the process.

Applicator and Insertion

Figure 10A:
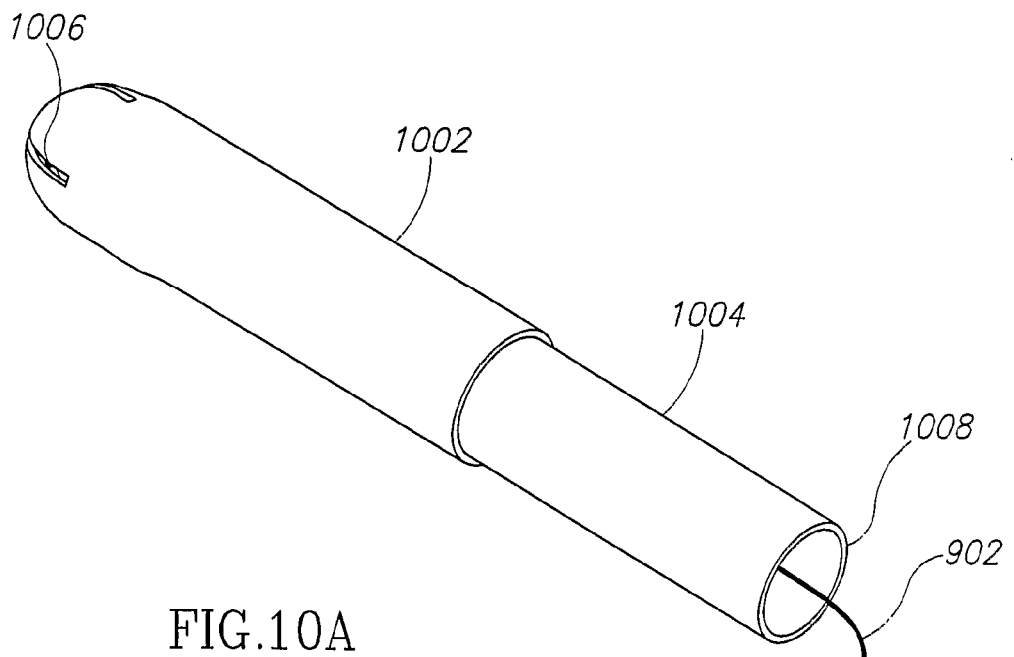
FIG. 10A is a perspective view of an applicator in an exemplary embodiment of the invention.
Figure 11:
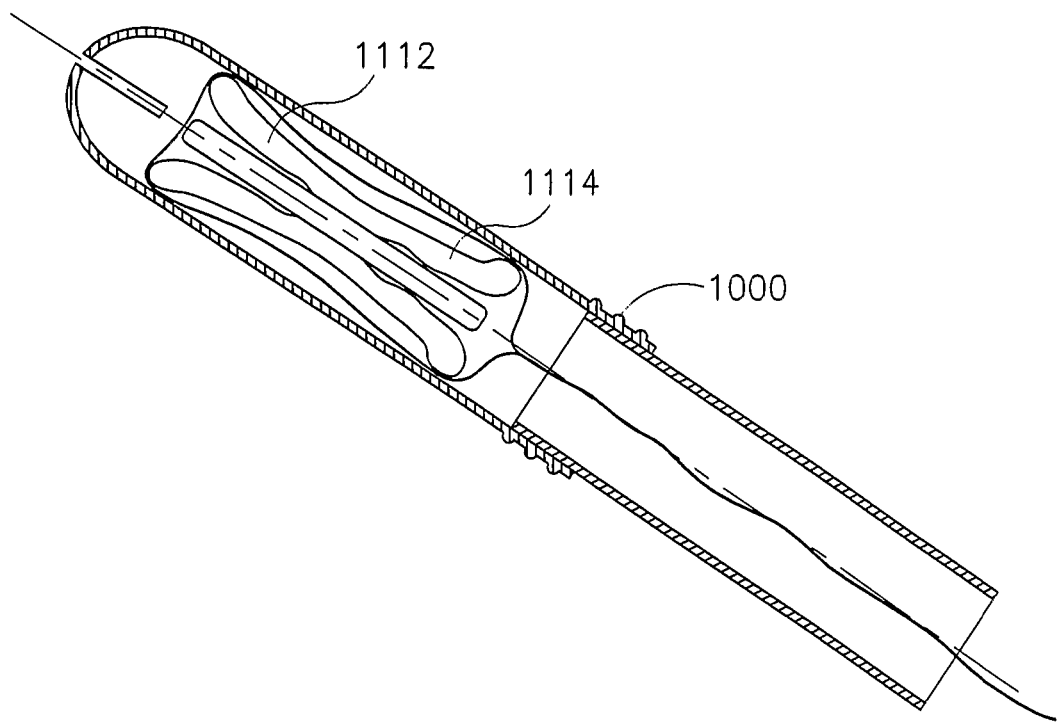
FIG. 11 is a cutaway view showing an incontinence prevention device in the applicator in an exemplary embodiment of the invention.

Referring now to FIG. 10A, an applicator is shown which serves for insertion of the device into the vagina. Insertion is accomplished using this applicator in a similar fashion to inserting a regular menstrual tampon. The incontinence device is kept within the distal end 1002 that is inserted into the vagina. When pushing the proximal end 1004, the device is pushed through the exit 1006, allowing for its immediate action once the applicator is removed from the vagina. It should be noted that in an exemplary embodiment of the invention, the exit 1006 remains closed until the proximal end 1004 is pushed and the incontinence device is forced out of the applicator. Optionally, the exit 1006 is flower-like. The string 902 is visible, protruding out of the opening 1008 of the proximal end 1004. A cutaway view of the applicator 1000 is shown in FIG. 11. When the device is still within the applicator 1000, its flexible arms 1112 and 1114 converge towards the central axis, providing for a much smaller profile than in its deployed configuration and allowing for its insertion via a small diameter applicator.

Figure 10B:
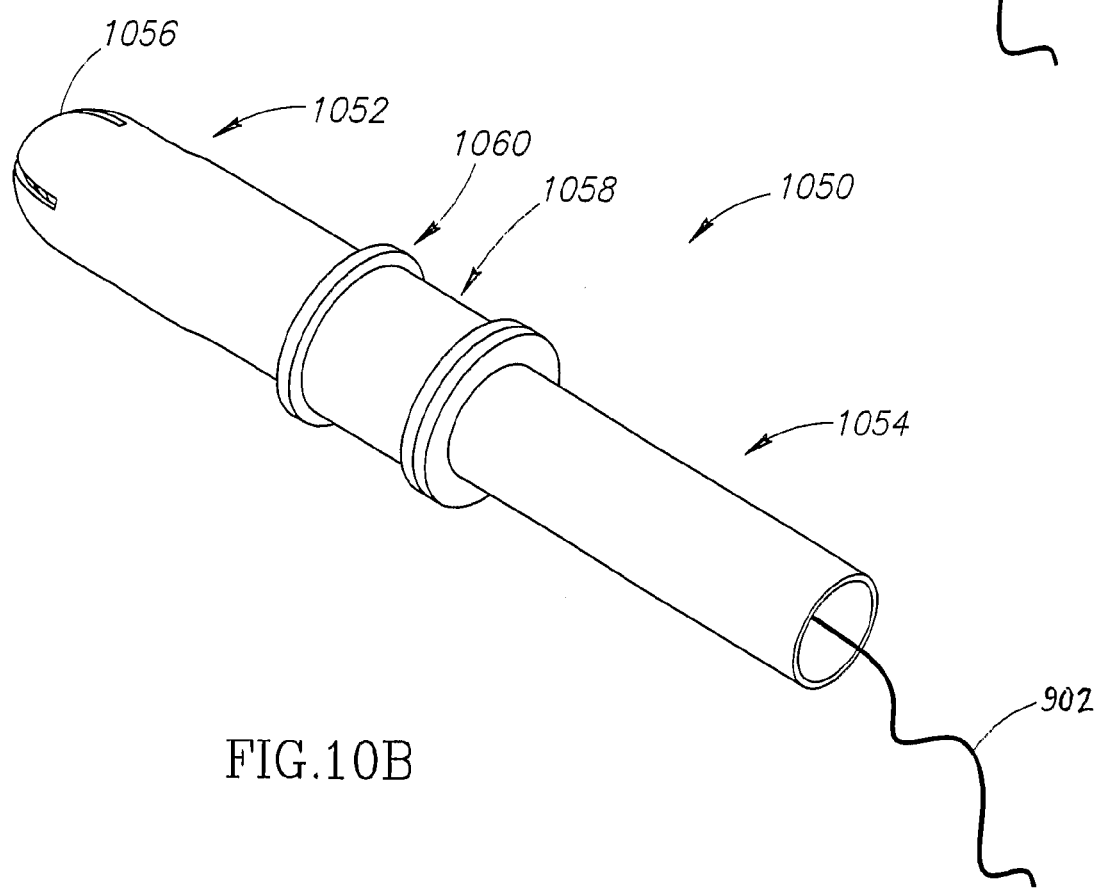
FIG. 10B is a perspective view of an alternate applicator in an exemplary embodiment of the invention.

An exemplary embodiment of the invention, an applicator 1050 is depicted in FIG. 10B. While applicator 1050 is equipped with a proximal end 1054, a distal end 1052 and an exit 1056, as with applicator 1000, this embodiment additionally includes a stopper 1058 which is positioned along applicator 1050 such that when stopper 1058 is grasped by a user upon insertion and applicator 1050 is advanced into the vagina up to the distal lip 1060 of stopper 1058, deployment of a device located within applicator 1050 is at an appropriate depth within the vagina to render effective treatment. Deployment of a device using this embodiment of an applicator is carried out in a manner similar to that described above, with the addition of using stopper 1058 for convenient depth measurement. Optionally, the stopper can be provided with selectable positions corresponding to different sized women, for personalization In some embodiments of the invention, an applicator is used which conveniently positions an incontinence treatment device for insertion into a vagina. For example, any of the devices described herein can be positioned on or in an applicator in a collapsed and/or folded configuration ready to be inserted into a vagina. In an exemplary embodiment of the invention, the device would be inserted into the vagina using the applicator, and then would be allowed to spring into an expanded shape by releasing the mechanism holding the device in a collapsed configuration. In an exemplary embodiment of the invention, a releasable knot is tied around the device using the device displacer, the knot bring released once the device is inserted into the vagina and the device displacer being located in an accessible place so that the device displacer can be used for removal of the device.

In an exemplary embodiment of the invention, the removal string is used to hold the anchor arms in a low profile condition until deployment by tying them together. Optionally, the removal string ties the anchor arms together in an easy-to-release knot which when the string is pulled on after device insertion, the knot releases and allows the anchor legs to spring into position. In an exemplary embodiment of the invention, the removal string then protrudes from or remains in the vicinity of the vaginal opening to allow for device removal at a later time. Optionally, the arms of the device are provided with slots for accommodating a string for tying the arms together. In some embodiments of the invention, the slots are reinforced to prevent the string from damaging the device while it is in storage, prior to use.

Figure 12A:
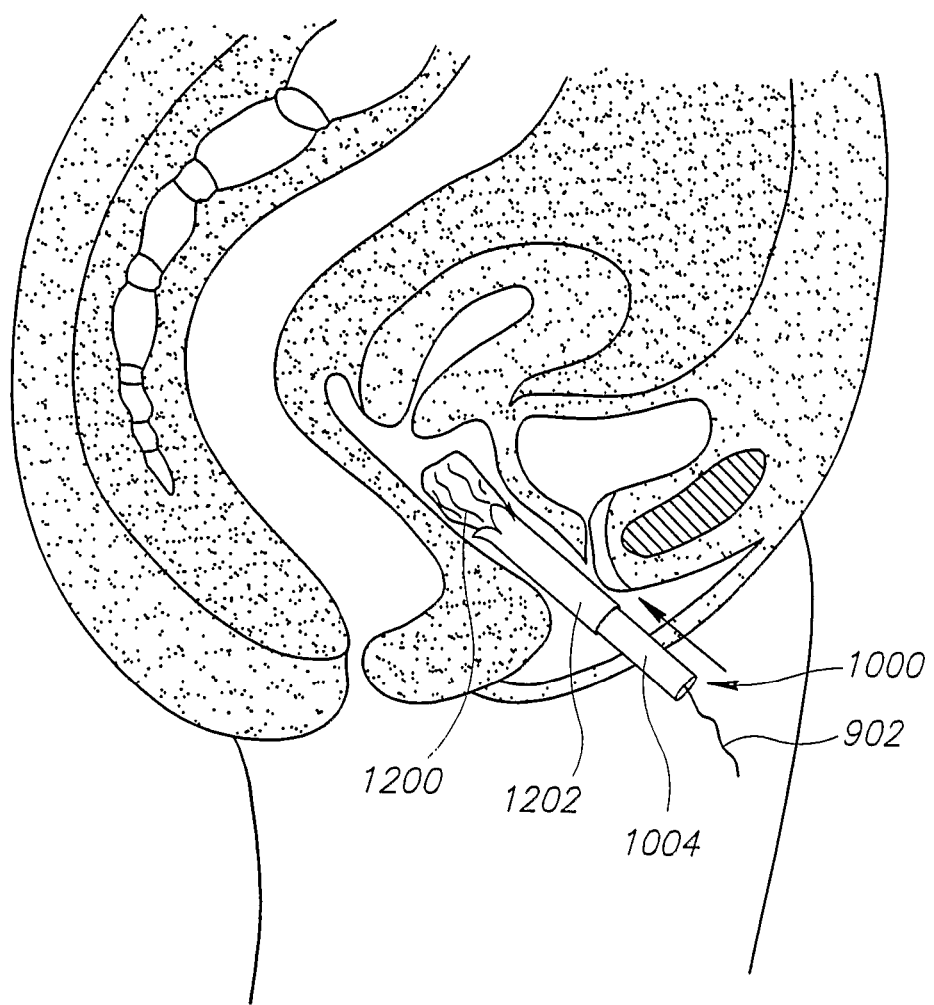
FIG. 12A is a view of the female pelvic region showing an incontinence device being deployed in accordance with an exemplary embodiment of the invention.

Referring now to FIG. 12A, the applicator 1000 is seen being inserted into the vagina for deployment of the incontinence device located within. The proximal end 1004 portion of the applicator 1000 is partially pushed towards the distal end 1002 and the anchor portion of the incontinence device 1200 has deployed into the vagina. Continued pushing of the proximal end 1004 towards the distal end 1002 will result in the device 1200 being completely free of the applicator 1000. Upon complete deployment of the device 1200, the applicator 1000 is removed from the vagina, leaving the device is in situ. The device 1200 naturally gravitates towards the proper therapeutic position due to the shape of the device and its compatibility with the internal structures present within the vagina. For example, in some exemplary embodiments of the invention, the support arms are adapted to fit within the creases which can be found on either side of the urethra. The naturally tendency for the support arms is to settle in the creases. Not coincidentally, in some embodiments of the invention the device is designed to render urethral support from such a position. As a corollary to the above, once the device has settled into position, it becomes resistant to unwanted motion, due to its fit into the geography of the vagina. In an exemplary embodiment of the invention, the device displacer 902 stays connected to the device 1200 throughout. Optionally, an applicator is not used to deploy the device 1200 in the vagina.

Figure 12B:
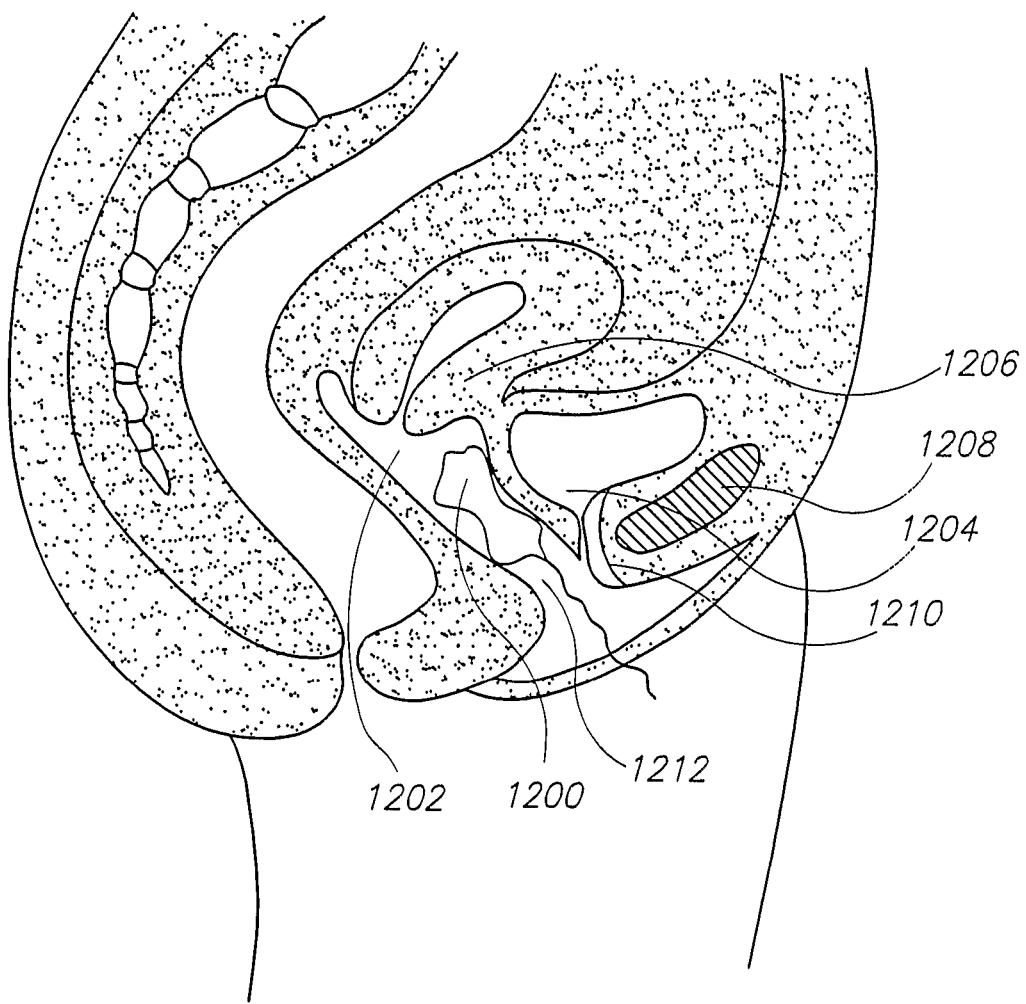
FIG. 12B is an illustration of the female pelvic region showing an incontinence device in situ in an exemplary embodiment of the invention.

In an exemplary embodiment of the invention, after insertion, the flexible arms of the device 1200 gain their pre-intended tension and enlarge the diameter of the device within the vagina 1202, depicted in FIG. 12B. The device anchors itself under the bladder 1204 between the uterine cervix 1206 and the pubic bone 1208, supporting the mid-urethra 1210. The string 902 optionally protrudes out of the vaginal introitus 1212, as with the regular menstrual tampon, allowing for removal. While the device 1200 is shown with a cover in FIG. 12B, it should be understood that a cover is only optional depending on the needs of the individual patient.

Figure 12C:
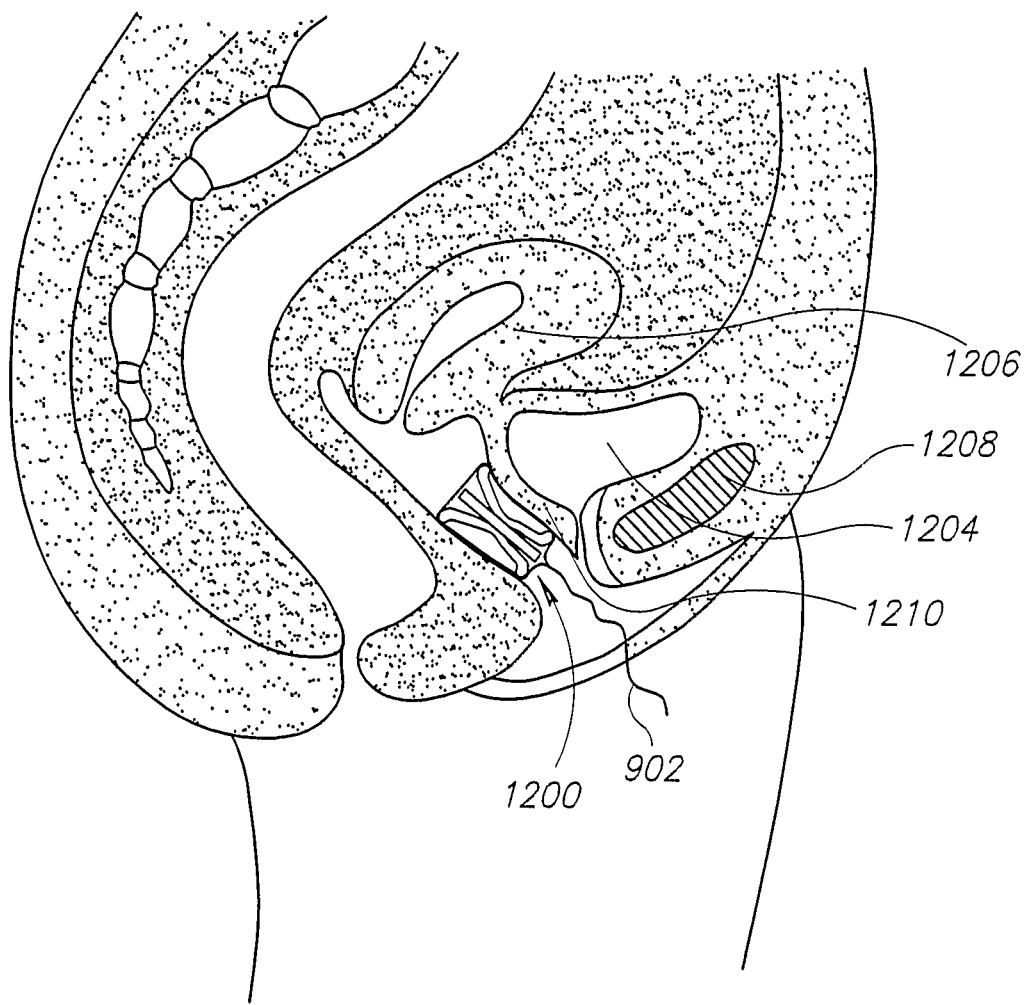
FIG. 12C is an up close illustration of an incontinence device in situ in accordance with an exemplary embodiment of the invention.

An exemplary embodiment of the invention is shown in the proper position for rendering incontinence treatment in FIG. 12C. FIG. 12C is a closer view of the device in situ, along with a cutaway of the cover, which shows the internal support structure within. The device 1200 is positioned underneath the mid-urethra 1210 and between the uterine cervix 1206 and the pubic bone 1208 as described above. It should be noted that in an exemplary embodiment of the invention, the device does not exert substantial affirmative pressure on the urethra. Rather, it acts as a support when the urethra moves downward due to a stressful event, such as coughing. In addition to the natural tenting tendency of the vaginal wall to provide support, the cover is optionally utilized as a "hainmock" like support, being suspended between the arms of the device 1200.

Figure 12D:
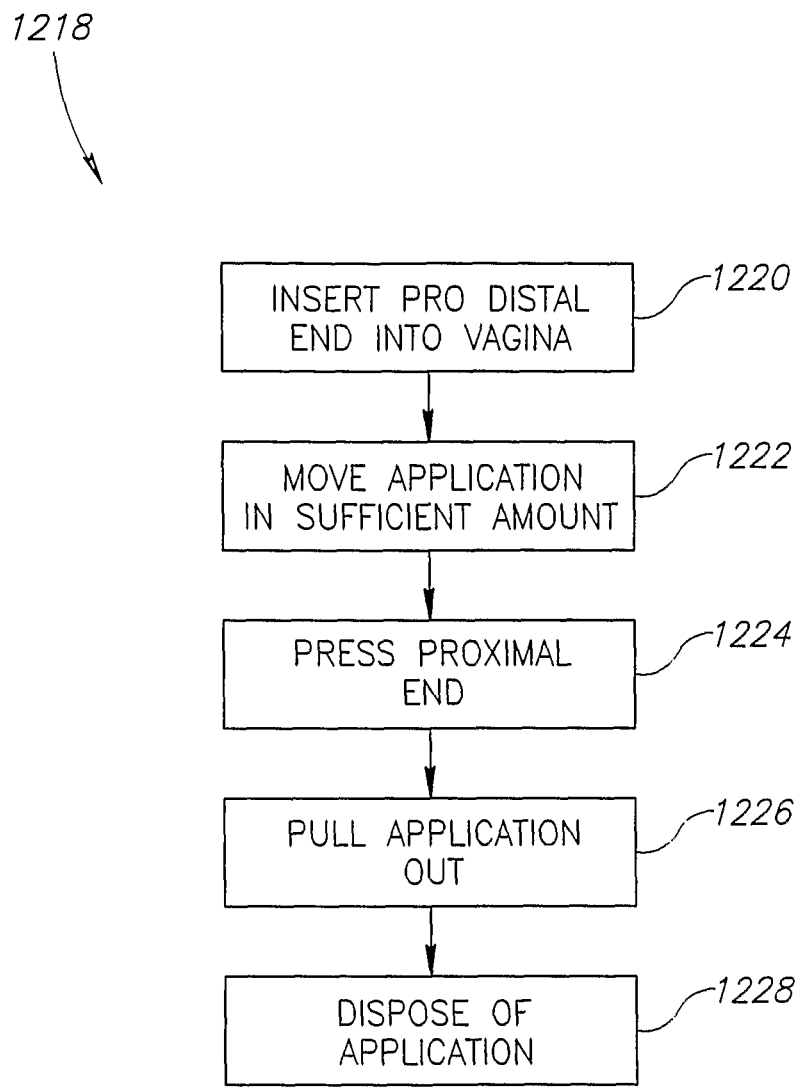
FIG. 12D is a flowchart depicting the insertion process in accordance with an exemplary embodiment of the invention.

Referring now to FIG. 12D, a flowchart 1218 is depicted which describes the process of inserting an incontinence device in accordance with an exemplary embodiment of the invention. At action 1220, the distal end 1002 of the applicator 1000 is inserted into the vaginal opening. It should be noted that in an exemplary embodiment of the invention, the applicator can be inserted at any rotational angle relative to the vaginal opening. The applicator 1000 is pushed into the vagina at action 1222 by the user in an amount sufficient to adequately deploy the incontinence device. The proximal end 1004 is then pushed at action 1224 towards the distal end 1002 while substantially holding the distal end 1002 steady. The proximal end 1004 thus acts as a "plunger" which forces the device out of the applicator through an exit 1006, as described in FIG. 10. Once the device is completely free of the applicator 1000, and has therefore deployed in the vagina, the applicator 1000 including the distal 1002 and proximal 1004 ends is removed from the vagina by the user at action 1226. The device displacer 902 remains attached to the device throughout the process and upon its conclusion protrudes from the vaginal opening. Optionally, the applicator 1000 is disposed of at action 1228.

Removal

Figure 13A:
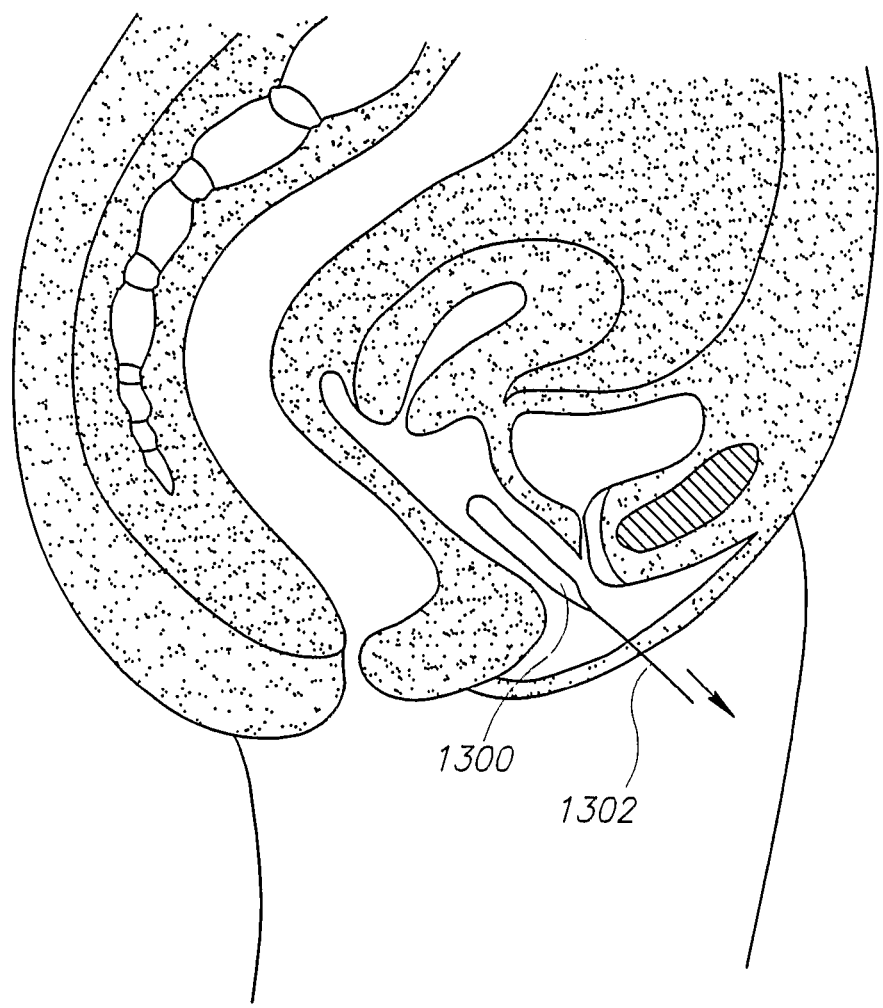
FIG. 13A is a view of the female pelvic region showing an incontinence device being removed in accordance with an exemplary embodiment of the invention.

Removal of the incontinence device is optionally assisted by the device displacer 1302, in accordance with an exemplary embodiment of the invention. FIG. 13A depicts a device 1300 being removed from the vagina. The basic process for device removal is explained above, however, it is important to note that downward force on the string 1302 causes the cover to reduce the device's profile within the vagina as described herein, allowing for easier removal. Removal of an optional device without a cover, but taking advantage of the same effect, is described below in conjunction with FIGS. 13C and D.

Figure 13B:
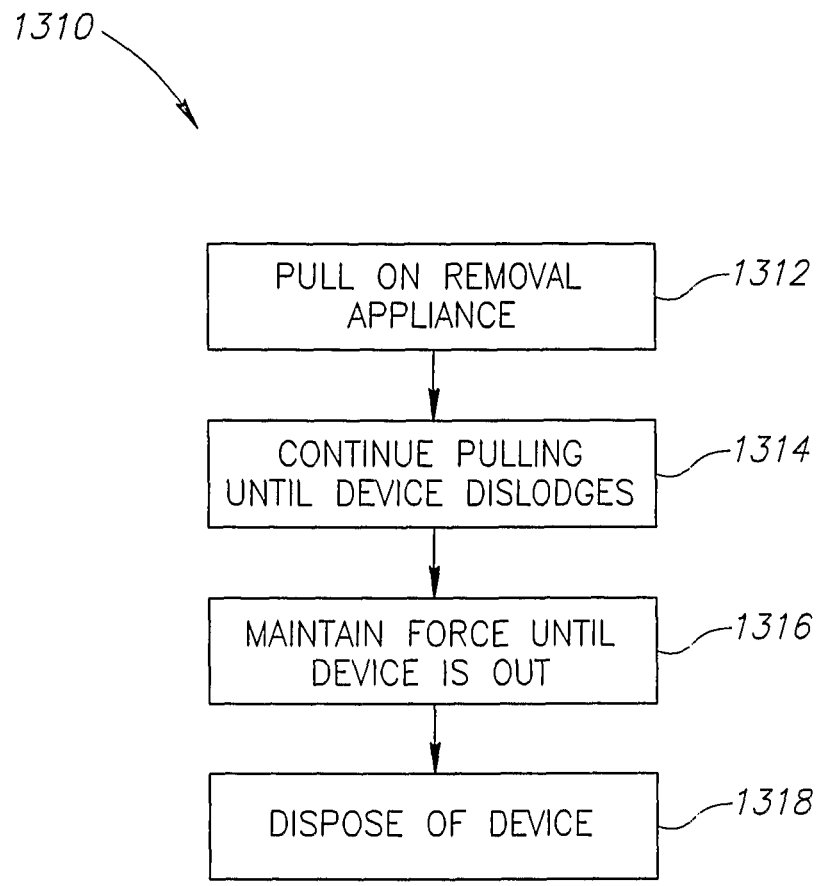
FIG. 13B is a flowchart depicting the removal process in accordance with an exemplary embodiment of the invention.

Referring now to FIG. 13B, a flowchart 1310 is depicted which describes the process of removing the device from the vagina. At action 1312, the user locates the device displacer and begins to exert force on the device displacer away from the vaginal opening. This tension on the device displacer causes the cover of the device to apply pressure to the arms of the device. As the arms collapse towards the central axis of the device, it inherently reduces its diameter. At action 1314, removing force is continually exerted on the device displacer as the device begins to dislodge from the vagina. The user maintains this force at action 1316 until the device is free of the vagina and removed from the user. Optionally, the device is disposed of at action 1318.

Optional Embodiment for Easy Removal

Figure 13C:
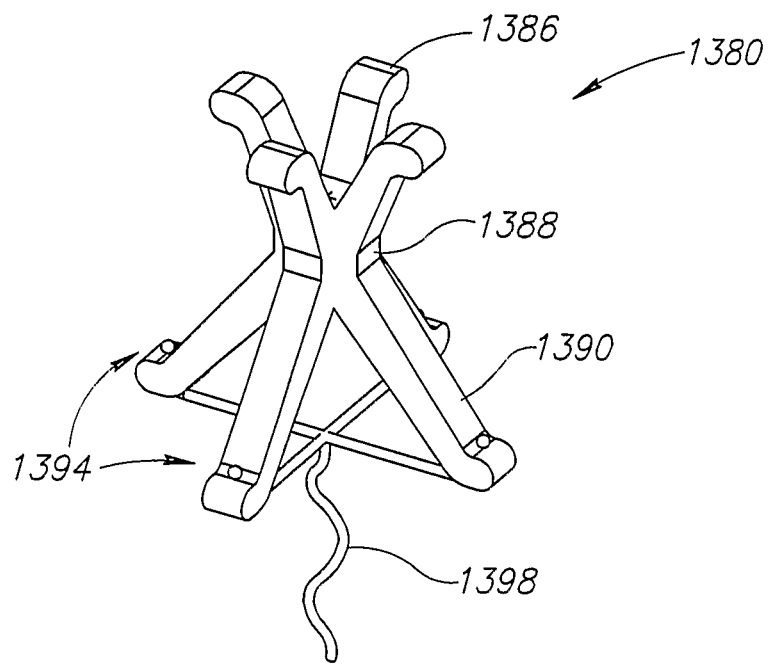
FIG. 13C is a perspective view of an optional internal structure with a retracting harness affixed to the support arms in an exemplary embodiment of the invention; and, FIG. 13D is a perspective view of an optional internal structure when retracting force is applied to the retraction harness in an exemplary embodiment of the invention.
Figure 13D:
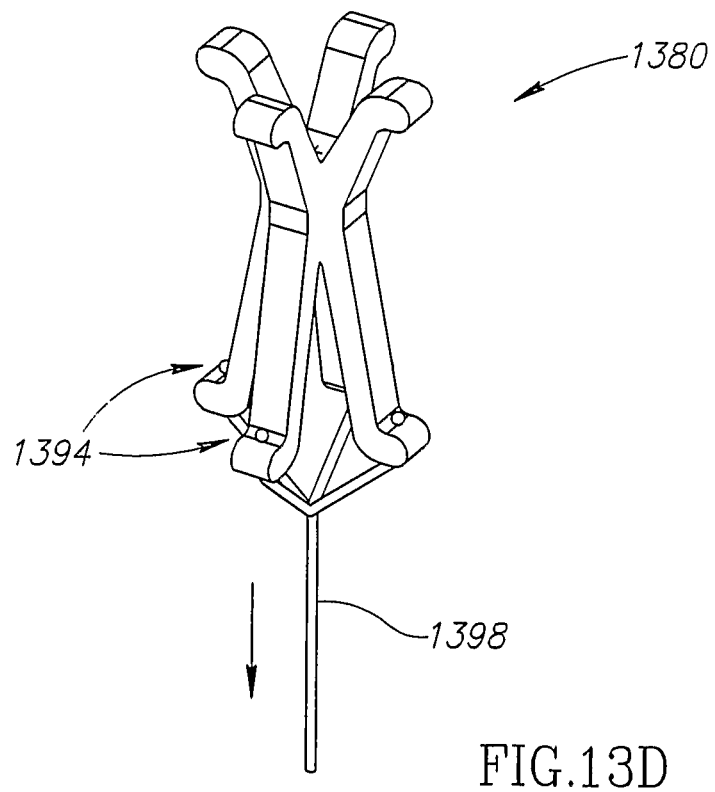

In an exemplary embodiment of the invention, a device 1380 for treating incontinence is provided which is adapted to be easily removed from the vagina. Depicted in FIG. 13C is an incontinence device generally comprised of an anchoring section 1386, a support section 1390 and a node 1388. A device displacer, such as a string 1398 is directly attached to the support element arms 1394 of the device. It can be seen in FIG. 13D that when downward force (i.e. force towards the vaginal opening) is applied, the support element arms 1394 collapse towards the central axis of the device 1380. Optionally, the juncture between the arms 1394 and the string is reinforced to prevent damage to the arms from the downward, removing force. As the diameter of the device gets smaller through additional exerted force and arm 1394 collapse, it gets easier to pull the device 1380 out of the vagina. In addition, use of the device displacer allows the woman to remove the device 1380 in a non-invasive and sanitary manner, without touching herself. It should be noted that this technique will work with rigid or flexible support element arms 1394. For example in the case of rigid arms, as long as the node 1388 is constructed of a flexible material, force on the arms 1394 will result in the node 1388 absorbing the stress applied to the rigid arms, allowing for the arms to collapse towards the central axis. In some embodiments of the invention, the tips of the arms are not pointed outwards from the central axis of the device allowing for easier removal because there is less friction between the device and the vaginal walls.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

What is claimed:

1. An apparatus arranged around a central axis for treating urinary incontinence said apparatus being sized and shaped for human intra-vaginal insertion, comprising:
    a node rotationally symmetrically located around the central axis thereof, said central axis being along a long axis of said apparatus and said apparatus configured so that said long axis lies along a vagina when inserted therein;
    a support section adapted for providing urethral support attached to said node using a plurality of outwardly extending arms;
    an extending insert adapted to increase the diameter of said support section by outwardly urging the arms;
    on anchoring section adapted for resisting movement of said apparatus attached to said node, when in said vagina; and,
    a separate cover configured to provide urethral support, thereby applying support to said urethra only during an increase in intra-abdominal pressure,
wherein said node is no longer than 30% of the entire length of said apparatus comprising said node, support section and said anchoring section together.

2. An apparatus of claim 1 wherein said cover substantially encapsulates said support section and said extending insert.

3. An apparatus of claim 1 further comprising a device displacer.

4. An apparatus of claim 3 wherein said device displacer is attached to said support section.

5. An apparatus of claim 1 further comprising an applicator adapted to insert said apparatus into a vagina.

* * * * *